(12) United States Patent
You et al.

(10) Patent No.: US 12,740,898 B2
(45) Date of Patent: Sep. 22, 2026

(54) MULTI-LAYER ABSORBENT CORES AND METHODS OF MANUFACTURE

(71) Applicant: Kimberly-Clark Worldwide, Inc., Neenah, WI (US)

(72) Inventors: Kueyoung You, Seongnam-si (KR); Minjae Lee, Yongin-si (KR); Sanghee Ra, Gwangjin-gu (KR); Somyong Song, Suseong-gu (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 478 days.

(21) Appl. No.: 17/626,203

(22) PCT Filed: Jul. 12, 2019

(86) PCT No.: PCT/US2019/041536

§ 371 (c)(1),
(2) Date: Jan. 11, 2022

(87) PCT Pub. No.: WO2021/010939

PCT Pub. Date: Jan. 21, 2021

(65) Prior Publication Data

US 2022/0241119 A1 Aug. 4, 2022

(51) Int. Cl.
*A61F 13/15* (2006.01)
*A61F 13/53* (2006.01)
(Continued)

(52) U.S. Cl.
CPC .. *A61F 13/15707* (2013.01); *A61F 13/15658* (2013.01); *A61F 13/15699* (2013.01);
(Continued)

(58) Field of Classification Search
CPC .......... A61F 13/15707; A61F 13/15658; A61F 13/15699; A61F 2013/53051;
(Continued)

(56) References Cited

U.S. PATENT DOCUMENTS 5,019,069 A 5/1991 Klemp
5,211,641 A 5/1993 Roos et al.
(Continued)

FOREIGN PATENT DOCUMENTS

CA 2248633 A1 3/2000
CN 1158558 A 9/1997
(Continued)

OTHER PUBLICATIONS

Mölnlycke, "Mölnlycke Health Care", http://www.molnlycke.us/see-the-proof/patented-design/5-unique-layers/.
(Continued)

*Primary Examiner* — Rebecca E Eisenberg
*Assistant Examiner* — Gabriella E Burnette
(74) *Attorney, Agent, or Firm* — KIMBERLY-CLARK WORLDWIDE, INC.

(57) ABSTRACT

Multi-layered absorbent bodies and methods of manufacture are disclosed. A method of forming an absorbent body may comprise moving a first covering material in a machine direction, moving a reinforcing material in the machine direction and combining the reinforcing material with the first covering material, the reinforcing material having a top side and a bottom side, applying absorbent material comprising superabsorbent particles to the top side of the reinforcing material, moving a second covering material in the machine direction and combining the second covering material with the first covering material and the reinforcing material to form a laminate structure of the first covering material, the reinforcing material, and the second covering material, with the first covering material disposed underneath the reinforcing material and the second covering material disposed on top of the reinforcing material, and embossing the laminate structure.

19 Claims, 9 Drawing Sheets

(51) Int. Cl.
*A61F 13/534* (2006.01)
*B31F 1/07* (2006.01)
*B31F 5/04* (2006.01)

(52) U.S. Cl.
CPC .................. *B31F 1/07* (2013.01); *B31F 5/04* (2013.01); *A61F 2013/53051* (2013.01); *A61F 2013/53463* (2013.01); *B31F 2201/0733* (2013.01); *B31F 2201/0738* (2013.01); *B31F 2201/0741* (2013.01)

(58) Field of Classification Search
CPC .......... A61F 2013/53463; A61F 2013/530481; A61F 13/533; A61F 13/536; B31F 1/07; B31F 5/04; B31F 2201/0733; B31F 2201/0738; B31F 2201/0741; B31F 5/008; A61L 15/60
See application file for complete search history.

(56) References Cited

U.S. PATENT DOCUMENTS 5,248,309 A 9/1993 Serbiak et al.
5,248,524 A 9/1993 Soderlund
5,324,278 A 6/1994 Visscher et al.
5,380,310 A 1/1995 Mitrani
5,422,169 A * 6/1995 Roe ........................ A61L 15/18 604/378
5,423,786 A 6/1995 Fung et al.
5,423,787 A 6/1995 Kjellberg
5,429,627 A 7/1995 Johnson et al.
5,441,442 A 8/1995 Haisma et al.
5,447,507 A 9/1995 Yamamoto
5,447,677 A 9/1995 Griffoul et al.
5,451,442 A 9/1995 Pieniak et al.
5,454,800 A 10/1995 Hirt et al.
5,460,623 A 10/1995 Emenaker et al.
5,556,392 A 9/1996 Koczab
5,562,646 A 10/1996 Goldman et al.
5,611,879 A 3/1997 Morman
5,649,916 A 7/1997 Dipalma et al.
5,674,214 A 10/1997 Visscher et al.
5,722,967 A 3/1998 Coles
5,728,084 A 3/1998 Palumbo et al.
5,733,274 A 3/1998 Osborn
5,769,836 A 6/1998 Klemp
5,776,121 A 7/1998 Roe et al.
5,821,179 A 10/1998 Masaki et al.
5,897,544 A 4/1999 Ronnberg
5,900,109 A 5/1999 Sanders et al.
5,910,137 A 6/1999 Clark et al.
6,024,822 A 2/2000 Alper et al.
6,050,984 A 4/2000 Fujioka et al.
6,068,620 A 5/2000 Chmielewski
6,140,550 A 10/2000 Beihoffer et al.
6,160,197 A 12/2000 Lassen et al.
6,162,959 A 12/2000 O'Connor
6,170,393 B1 * 1/2001 Hook ................ A61F 13/15707 101/6
6,329,565 B1 12/2001 Dutkiewicz et al.
6,372,952 B1 4/2002 Lash et al.
6,417,120 B1 * 7/2002 Mitchler .................. D04H 1/56 428/326
6,475,199 B1 11/2002 Gann et al.
6,506,959 B2 1/2003 Hamajima et al.
6,566,578 B1 5/2003 Glaug et al.
6,569,137 B2 5/2003 Suzuki et al.
6,602,234 B2 8/2003 Klemp et al.
6,613,955 B1 9/2003 Lindsay et al.
6,632,209 B1 10/2003 Chmielewski
6,638,260 B2 10/2003 Mishima
6,645,186 B2 11/2003 Otsubo
6,652,499 B1 11/2003 Edgren et al.
6,666,851 B2 12/2003 Otsubo et al.
6,673,985 B2 1/2004 Mizutani et al.
6,677,498 B2 1/2004 Chen et al.
6,689,416 B2 2/2004 Delzer et al.
6,733,484 B2 5/2004 Van Gompel et al.
6,790,798 B1 9/2004 Suzuki et al.
6,794,557 B1 9/2004 Klemp et al.
6,797,360 B2 9/2004 Varona
6,822,135 B2 11/2004 Soerens et al.
6,852,101 B2 2/2005 Damaghi et al.
6,878,138 B2 4/2005 Tsuji et al.
6,888,044 B2 5/2005 Fell et al.
6,902,552 B2 6/2005 Vangompel et al.
6,955,667 B1 10/2005 Tanaka et al.
6,964,803 B2 11/2005 Krautkramer et al.
7,008,408 B2 3/2006 Otsubo
7,022,114 B2 4/2006 Fernfors et al.
7,090,667 B2 8/2006 Fell et al.
7,108,916 B2 9/2006 Ehrnsperger et al.
7,121,818 B2 10/2006 Driskell
7,169,136 B2 1/2007 Otsubo et al.
7,172,583 B2 2/2007 Otsubo et al.
7,226,437 B2 6/2007 Sasaki et al.
7,232,300 B2 6/2007 Walter et al.
7,247,215 B2 7/2007 Schewe et al.
7,294,591 B2 11/2007 Soerens et al.
7,326,193 B2 2/2008 Shimada et al.
7,344,522 B2 3/2008 Suzuki et al.
7,378,566 B2 5/2008 Soerens et al.
7,458,960 B2 12/2008 Otsubo et al.
7,520,874 B2 4/2009 Koyama et al.
7,615,039 B2 11/2009 Rosenfeld et al.
7,662,460 B2 2/2010 Herfert et al.
7,695,461 B2 4/2010 Rosenfeld et al.
7,708,727 B2 5/2010 Woltman et al.
7,717,150 B2 5/2010 Manabe et al.
7,722,590 B2 5/2010 Tsuji et al.
7,727,212 B2 6/2010 Sakai et al.
7,767,875 B2 8/2010 Olson et al.
7,772,457 B2 8/2010 Ohtsuka et al.
7,811,270 B2 10/2010 Rosenfeld et al.
7,842,021 B2 11/2010 Wood et al.
7,847,145 B2 12/2010 Kurita et al.
7,855,314 B2 12/2010 Hanao et al.
7,884,259 B2 2/2011 Hanao et al.
7,887,527 B2 2/2011 Hayashi et al.
7,935,299 B2 5/2011 Walsh et al.
7,955,536 B2 6/2011 Sawyer et al.
7,959,622 B2 6/2011 Kudo et al.
8,163,124 B2 4/2012 Moriura et al.
8,173,858 B2 5/2012 Kuroda et al.
8,178,035 B2 5/2012 Edvardsson et al.
8,182,736 B2 5/2012 Edvardsson
8,183,430 B2 5/2012 Hakansson et al.
8,207,395 B2 6/2012 Soerens et al.
8,251,966 B2 8/2012 Kudo et al.
8,277,432 B2 10/2012 Bergstrom et al.
8,361,047 B2 1/2013 Mukai et al.
8,466,334 B2 6/2013 Takeuchi et al.
8,480,387 B2 7/2013 Alkmin et al.
8,556,875 B2 10/2013 Takahashi et al.
8,591,490 B2 11/2013 Kudo et al.
8,616,867 B2 12/2013 Brown et al.
8,691,040 B2 4/2014 Yamamoto
8,754,286 B2 6/2014 Bergstrom et al.
8,852,381 B2 10/2014 Nhan et al.
8,859,844 B2 10/2014 Takeuchi et al.
8,871,123 B2 10/2014 de Carvalho et al.
8,968,263 B2 3/2015 Watabe et al.
8,998,871 B2 4/2015 Kuroda et al.
9,056,034 B2 6/2015 Akiyama
9,066,838 B2 6/2015 Hippe et al.
9,072,634 B2 7/2015 Hundorf et al.
9,216,116 B2 12/2015 Roe et al.
9,238,089 B2 1/2016 Chmielewski et al.
9,326,896 B2 5/2016 Schäfer et al.
9,375,506 B2 6/2016 Konishi et al.
9,468,566 B2 10/2016 Rosati et al.
9,549,858 B2 1/2017 Yang
9,730,843 B2 8/2017 Rosati et al.
9,750,651 B2 9/2017 Bianchi et al.

(56) References Cited

U.S. PATENT DOCUMENTS 9,757,284 B2 9/2017 Tsang et al.
9,782,305 B2 10/2017 Mukai et al.
9,782,306 B2 10/2017 Tsang et al.
9,782,307 B2 10/2017 Blessing et al.
9,789,009 B2 10/2017 Joseph
9,789,011 B2 10/2017 Roe et al.
9,789,012 B2 10/2017 Chmielewski et al.
9,789,014 B2 10/2017 Wright et al.
9,889,050 B2 2/2018 Arayama et al.
9,913,763 B2 3/2018 Ryu et al.
10,071,002 B2 9/2018 Bianchi et al.
10,098,795 B2 10/2018 Mukai et al.
10,137,039 B2 11/2018 Stelzig et al.
10,137,040 B2 11/2018 Ehrnsperger et al.
10,201,462 B2 2/2019 Wright et al.
10,441,481 B2 10/2019 Bianchi et al.
10,456,305 B2 10/2019 Ehrnsperger et al.
10,543,130 B2 1/2020 Raycheck et al.
10,675,191 B2 6/2020 Suzuki et al.
10,687,994 B2 6/2020 Chmielewski et al.
2001/0006089 A1* 7/2001 Ando ................ A61F 13/15658 427/2.3
2001/0039405 A1* 11/2001 Keuhn, Jr. ........ A61F 13/15203 604/385.01
2002/0007165 A1 1/2002 Proglhof et al.
2002/0133131 A1 9/2002 Rangachari et al.
2003/0060792 A1 3/2003 Harriz et al.
2003/0084983 A1 5/2003 Rangachari et al.
2003/0098115 A1* 5/2003 Dodge, II ................ D04H 3/16 156/167
2003/0129915 A1 7/2003 Harriz
2003/0135176 A1 7/2003 Delzer et al.
2003/0143376 A1 7/2003 Toyoshima et al.
2003/0187413 A1 10/2003 Fell
2003/0236512 A1 12/2003 Baker
2004/0054342 A1 3/2004 Newbill et al.
2004/0126543 A1 7/2004 Potts et al.
2004/0253894 A1 12/2004 Fell et al.
2005/0124961 A1 6/2005 Morman et al.
2005/0186351 A1 8/2005 Fung et al.
2006/0004334 A1 1/2006 Schlinz et al.
2006/0020250 A1 1/2006 Chester et al.
2006/0040579 A1 2/2006 Sheldon et al.
2006/0058747 A1 3/2006 Nguyen et al.
2006/0184149 A1 8/2006 Kasai et al.
2006/0204723 A1 9/2006 Bentley et al.
2006/0206072 A1 9/2006 Malakouti et al.
2006/0206074 A1 9/2006 Bernal et al.
2006/0266467 A1 11/2006 Mlinar
2007/0142802 A1 6/2007 Suzuki
2007/0244455 A1 10/2007 Hansson et al.
2008/0082075 A1 4/2008 Morrell-Schwartz
2008/0167634 A1 7/2008 Kouta et al.
2009/0087636 A1 4/2009 Yasuda et al.
2010/0032860 A1 2/2010 Hernandez et al.
2011/0152809 A1 6/2011 Carlucci et al.
2011/0184365 A1 7/2011 Röttger et al.
2011/0313384 A1 12/2011 Akiyama
2012/0226253 A1 9/2012 Urushihara
2012/0232508 A1 9/2012 Urushihara
2012/0316524 A1 12/2012 Thomann et al.
2013/0174959 A1 7/2013 Kufner et al.
2013/0184666 A1 7/2013 Sasayama et al.
2014/0276510 A1 9/2014 Ducker et al.
2014/0308483 A1 10/2014 Li
2015/0045756 A1 2/2015 Wright et al.
2015/0065974 A1 3/2015 Michiels et al.
2015/0174280 A1 6/2015 Stelzig et al.
2015/0209196 A1 7/2015 Li
2015/0282992 A1* 10/2015 Deng .................... B29C 59/005 425/363
2015/0313769 A1 11/2015 Dahl et al.
2015/0342796 A1 12/2015 Bianchi et al.
2015/0342797 A1 12/2015 Jackels
2015/0342798 A1 12/2015 Jackels
2015/0342799 A1 12/2015 Michiels et al.
2015/0342801 A1 12/2015 Bianchi et al.
2016/0040337 A1 2/2016 Dutkiewicz et al.
2016/0158401 A1 6/2016 Tai et al.
2016/0235594 A1 8/2016 Ehrnsperger et al.
2016/0235595 A1 8/2016 Ehrnsperger et al.
2016/0235596 A1 8/2016 Ehrnsperger et al.
2016/0235603 A1 8/2016 Ehrnsperger et al.
2016/0235604 A1 8/2016 Ehrnsperger et al.
2016/0235605 A1 8/2016 Ehrnsperger et al.
2016/0270987 A1 9/2016 Stiehl et al.
2017/0056255 A1 3/2017 Fites et al.
2017/0102306 A1 4/2017 Dagher et al.
2017/0128276 A1 5/2017 Scaife
2017/0135870 A1 5/2017 Kamphus
2017/0135871 A1 5/2017 Kamphus
2017/0281423 A1 10/2017 Panayotova et al.
2017/0312145 A1 11/2017 Bianchi et al.
2017/0312146 A1 11/2017 Bianchi et al.
2017/0312147 A1 11/2017 Bianchi et al.
2018/0064583 A1 3/2018 Van De Maele
2018/0185203 A1 7/2018 Mukai et al.
2018/0207039 A1 7/2018 Kreuzer et al.
2018/0256415 A1 9/2018 Miao et al.
2018/0344541 A1 12/2018 Ito et al.
2019/0046368 A1 2/2019 Peri et al.
2019/0053956 A1 2/2019 Nakamura et al.
2019/0076307 A1 3/2019 Takashima et al.
2019/0358097 A1 11/2019 Chmielewski et al.
2020/0253796 A1 8/2020 Chmielewski et al.
2020/0337914 A1 10/2020 Onishi

FOREIGN PATENT DOCUMENTS

CN 1163100 A 10/1997
CN 1336868 A 2/2002
CN 1215825 C 8/2005
CN 200977230 Y 11/2007
CN 1676225 B 11/2010
CN 101061977 B 6/2011
CN 102438665 A 5/2012
CN 103007333 A 4/2013
CN 101641067 B 5/2013
CN 202984020 U 6/2013
CN 103300975 A 9/2013
CN 103491912 A 1/2014
CN 203417298 U 2/2014
CN 203436465 U 2/2014
CN 103637883 A 3/2014
CN 102361612 B 6/2014
CN 102573733 B 7/2014
CN 102573734 B 7/2014
CN 103892966 A 7/2014
CN 102083474 B 8/2014
CN 203790143 U 8/2014
CN 101849876 B 9/2014
CN 203815724 U 9/2014
CN 203885720 U 10/2014
CN 102781384 B 11/2014
CN 104161623 A 11/2014
CN 103282001 B 12/2014
CN 204016630 U 12/2014
CN 104394823 A 3/2015
CN 102700179 B 4/2015
CN 103327942 B 4/2015
CN 104540488 A 4/2015
CN 204260925 U 4/2015
CN 104602658 A 5/2015
CN 104605995 A 5/2015
CN 104723618 A 6/2015
CN 204501258 U 7/2015
CN 103006385 B 10/2015
CN 102378615 B 1/2016
CN 105530900 A 4/2016
CN 205163419 U 4/2016
CN 103249385 B 5/2016
CN 105722485 A 6/2016
CN 205286723 U 6/2016
CN 205359815 U 7/2016

(56) References Cited

FOREIGN PATENT DOCUMENTS

| | | | |
|---|---|---|---|
| CN | 105853068 | A | 8/2016 |
| CN | 205494179 | U | 8/2016 |
| CN | 103269664 | B | 9/2016 |
| CN | 103402470 | B | 10/2016 |
| CN | 106038084 | A | 10/2016 |
| CN | 103313683 | B | 2/2017 |
| CN | 106361506 | A | 2/2017 |
| CN | 205947928 | U | 2/2017 |
| CN | 205947929 | U | 2/2017 |
| CN | 104470477 | B | 4/2017 |
| CN | 106821603 | A | 6/2017 |
| CN | 106880445 | A | 6/2017 |
| CN | 206214292 | U | 6/2017 |
| CN | 106937903 | A | 7/2017 |
| CN | 106974774 | A | 7/2017 |
| CN | 107625583 | A | 1/2018 |
| CN | 107802410 | A | 3/2018 |
| CN | 207745262 | U | 8/2018 |
| CN | 109568012 | A | 4/2019 |
| CN | 109620550 | A | 4/2019 |
| CN | 109758305 | A | 5/2019 |
| CN | 209032878 | U | 6/2019 |
| CN | 209075162 | U | 7/2019 |
| CN | 110547917 | A | 12/2019 |
| CN | 110840657 | A | 2/2020 |
| CN | 212439076 | U | 2/2021 |
| DE | 3620077 | C2 | 2/1991 |
| DE | 202012013572 | U1 | 1/2018 |
| EP | 0348978 | A2 | 1/1990 |
| EP | 0442223 | B1 | 2/1995 |
| EP | 0606208 | B1 | 5/1996 |
| EP | 0549781 | B1 | 9/1996 |
| EP | 0768070 | A1 | 4/1997 |
| EP | 0746296 | B1 | 6/2001 |
| EP | 1032337 | B1 | 10/2004 |
| EP | 2591758 | A1 | 5/2013 |
| EP | 2679210 | A1 | 1/2014 |
| EP | 3047827 | B1 | 3/2018 |
| EP | 3042639 | B1 | 9/2018 |
| EP | 2656826 | B1 | 10/2018 |
| FR | 2604064 | B1 | 2/1991 |
| GB | 2246373 | A | 1/1992 |
| GB | 2272916 | A | 6/1994 |
| GB | 2306331 | A | 5/1997 |
| GB | 2366518 | A | 3/2002 |
| JP | 1993049658 | A | 3/1993 |
| JP | 1997313530 | A | 12/1997 |
| JP | 3145105 | B2 | 3/2001 |
| JP | 2004016373 | A | 1/2004 |
| JP | 2004329511 | A | 11/2004 |
| JP | 3607038 | B2 | 1/2005 |
| JP | 3705943 | B2 | 10/2005 |
| JP | 2006230714 | A | 9/2006 |
| JP | 3847680 | B2 | 11/2006 |
| JP | 3883915 | B2 | 2/2007 |
| JP | 4128029 | B2 | 7/2008 |
| JP | 4156171 | B2 | 9/2008 |
| JP | 4163133 | B2 | 10/2008 |
| JP | 4280187 | B2 | 6/2009 |
| JP | 4678632 | B2 | 4/2011 |
| JP | 4695332 | B2 | 6/2011 |
| JP | 4883924 | B2 | 2/2012 |
| JP | 4919734 | B2 | 4/2012 |
| JP | 5001099 | B2 | 8/2012 |
| JP | 2013042881 | A | 3/2013 |
| JP | 5175147 | B2 | 4/2013 |
| JP | 5329274 | B2 | 10/2013 |
| JP | 5372484 | B2 | 12/2013 |
| JP | 5374298 | B2 | 12/2013 |
| JP | 5789423 | B2 | 10/2015 |
| JP | 5926904 | B2 | 5/2016 |
| JP | 6062707 | B2 | 1/2017 |
| JP | 6073619 | B2 | 2/2017 |
| JP | 6074184 | B2 | 2/2017 |
| JP | 6148419 | B2 | 6/2017 |
| JP | 2017217468 | A | 12/2017 |
| JP | 6306450 | B2 | 4/2018 |
| JP | 2018050669 | A | 4/2018 |
| JP | 6382253 | B2 | 8/2018 |
| JP | 2018166941 | A | 11/2018 |
| JP | 6460828 | B2 | 1/2019 |
| JP | 6496567 | B2 | 4/2019 |
| JP | 2019141308 | A | 8/2019 |
| JP | 2019162300 | A | 9/2019 |
| JP | 2019187740 | A | 10/2019 |
| JP | 2019208849 | A | 12/2019 |
| JP | 2020000273 | A | 1/2020 |
| JP | 2020010851 | A | 1/2020 |
| WO | 2009150984 | A1 | 12/2009 |
| WO | 2012002557 | A1 | 1/2012 |
| WO | 2012105283 | A1 | 8/2012 |
| WO | 2012105284 | A1 | 8/2012 |
| WO | 2014084087 | A1 | 6/2014 |
| WO | 2015012155 | A1 | 1/2015 |
| WO | 2015129367 | A1 | 9/2015 |
| WO | 2015198662 | A1 | 12/2015 |
| WO | 2015198665 | A1 | 12/2015 |
| WO | 2016063638 | A1 | 4/2016 |
| WO | 2016104184 | A1 | 6/2016 |
| WO | 16115181 | A1 | 7/2016 |
| WO | 2017077750 | A1 | 5/2017 |
| WO | 2017110747 | A1 | 6/2017 |
| WO | 17171782 | A1 | 10/2017 |
| WO | 2018100650 | A1 | 6/2018 |
| WO | 2018112229 | A1 | 6/2018 |
| WO | 2018123684 | A1 | 7/2018 |
| WO | 2018173737 | A1 | 9/2018 |
| WO | 2019070009 | A1 | 4/2019 |
| WO | 2019092807 | A1 | 5/2019 |
| WO | 2019092810 | A1 | 5/2019 |
| WO | 2020117731 | A1 | 6/2020 |

OTHER PUBLICATIONS

Google, "Core Issues for Diapers: Thin is in", Sep. 28, 2015, https://index17.ch/en/news/core-issues-for-diapers-thin-is-in-195.

Edana, "Superabsorbent", https://www.edana.org/discover-nonwovens/how-they're-made/superabsorbents.

* cited by examiner 21
49
48
45
44
25
75
71
39
61
77
70
50
3
24
55
45
56
40
63
53
54
41
44
52
56
3
36
51
76
39
71
32
75
70
38
44
45
44
20
41
47
46
40
40
22
34
30
23

200'
203
203
204
205
212
213
244
211
215b
216b
240
202
202
240
215a
216a
209
210
201
201

MULTI-LAYER ABSORBENT CORES AND METHODS OF MANUFACTURE

TECHNICAL FIELD

The present disclosure is directed to absorbent bodies, and more particularly to layered absorbent bodies for use in, for example, absorbent articles.

BACKGROUND OF THE DISCLOSURE

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products.

One important component of many absorbent articles are the absorbent bodies, such as absorbent cores, contained in such articles. These absorbent bodies are generally responsible for capturing and retaining liquid bodily exudates, thereby preventing the exudates from leaking out of the absorbent article and further retaining the liquid away from a wearer's skin, which helps to promote the health of the skin. Advances in the structure and performance of absorbent bodies to produce thinner products which uptake liquid more quickly and leak less are a continued important area of market desire.

SUMMARY OF THE DISCLOSURE

The present disclosure is directed to absorbent bodies, and more particularly to layered absorbent bodies for use in, for example, absorbent articles.

In a first embodiment, a method of forming an absorbent body may comprise moving a first covering material in a machine direction, the first covering material having a top side and a bottom side, moving a reinforcing material in the machine direction and combining the reinforcing material with the first covering material, the reinforcing material having a top side and a bottom side, applying absorbent material comprising superabsorbent particles to the top side of the reinforcing material, moving a second covering material in the machine direction, the second covering material having a top side and a bottom side, and combining the second covering material with the first covering material and the reinforcing material to form a laminate structure of the first covering material, the reinforcing material, and the second covering material, with the first covering material disposed underneath the reinforcing material and the second covering material disposed on top of the reinforcing material, and embossing the laminate structure.

In a second embodiment, an absorbent body may comprise a top, liquid permeable covering material, a bottom covering material, a reinforcing material disposed between the top covering material and the bottom covering material, and superabsorbent material disposed within the reinforcing material in a pattern of high-SAM concentration regions and low-SAM concentration regions.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

Figure 1:
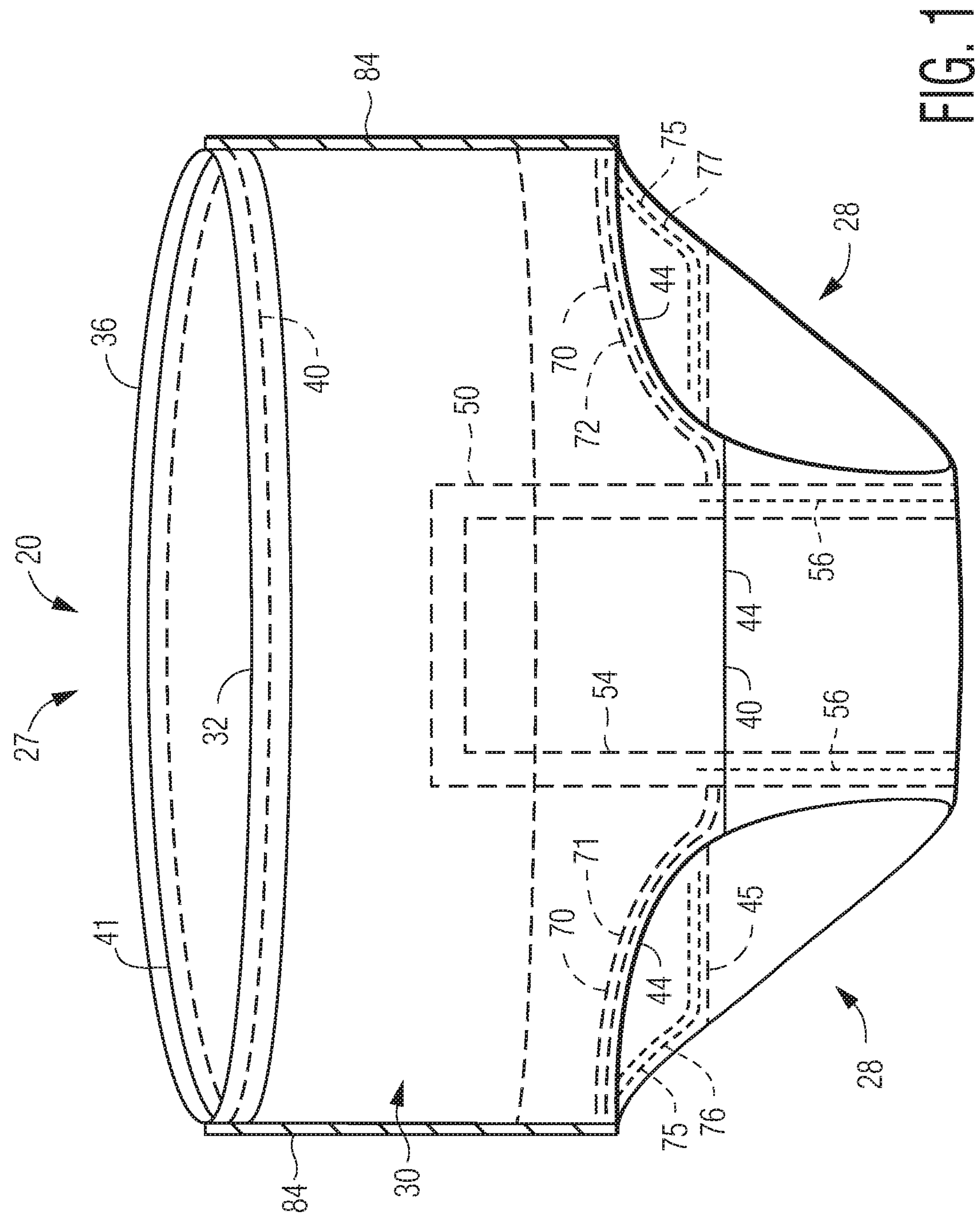
FIG. 1 is a perspective view of an exemplary absorbent article in a closed configuration, according to aspects of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The following description should be read with reference to the drawings in which similar elements in different drawings are numbered the same. The description and the drawings, which are not necessarily to scale, depict illustrative embodiments and are not intended to limit the scope of the disclosure.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including"

and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Within the context of this specification, each term or phrase below will include the following meaning or meanings. Additional terms are defined elsewhere in the specification.

"Absorbent article" or "absorbent garment" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, and incontinence products, and the like without departing from the scope of the present disclosure.

"Airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

"Bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

"Bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

"Coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 50 percent, more preferably by at least 100 percent, and still more preferably by at least 300 percent of its relaxed length and recover, upon release of an applied force, at least 50 percent of its elongation.

"Fibrous absorbent material" or "absorbent fibers" refers herein to natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber.

"Layer" when used in the singular can have the dual meaning of a single element or a plurality of elements.

"Machine direction" (MD) refers to the length of a fabric in the direction in which it is produced, as opposed to a "cross-machine direction" (CD) which refers to the width of a fabric in a direction generally perpendicular to the machine direction.

"Member" when used in the singular can have the dual meaning of a single element or a plurality of elements.

"Nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc.

"Spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

"Superabsorbent polymer," "superabsorbent material" "SAP", or "SAM" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent garments in particle or fibrous form or as a coating or another material or fiber.

"Particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod like polyhedral, spherical or semi-spherical, rounded or semi-rounded, angular, irregular, et cetera.

"Particulate superabsorbent polymer" and "particulate superabsorbent polymer composition" refer to the form of superabsorbent polymer and superabsorbent polymer compositions in discrete form, wherein the "particulate superabsorbent polymer" and "particulate superabsorbent polymer compositions" may have a particle size of less than 1000 μm, or from about 150 μm to about 850 μm.

"Polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

"Percent (%) by weight" or "% wt" as used herein and referring to components of the dry particulate superabsorbent polymer composition, is to be interpreted as based on the weight of the dry superabsorbent polymer composition, unless otherwise specified herein.

These terms may be defined with additional language in the remaining portions of the specification.

Figure 2:
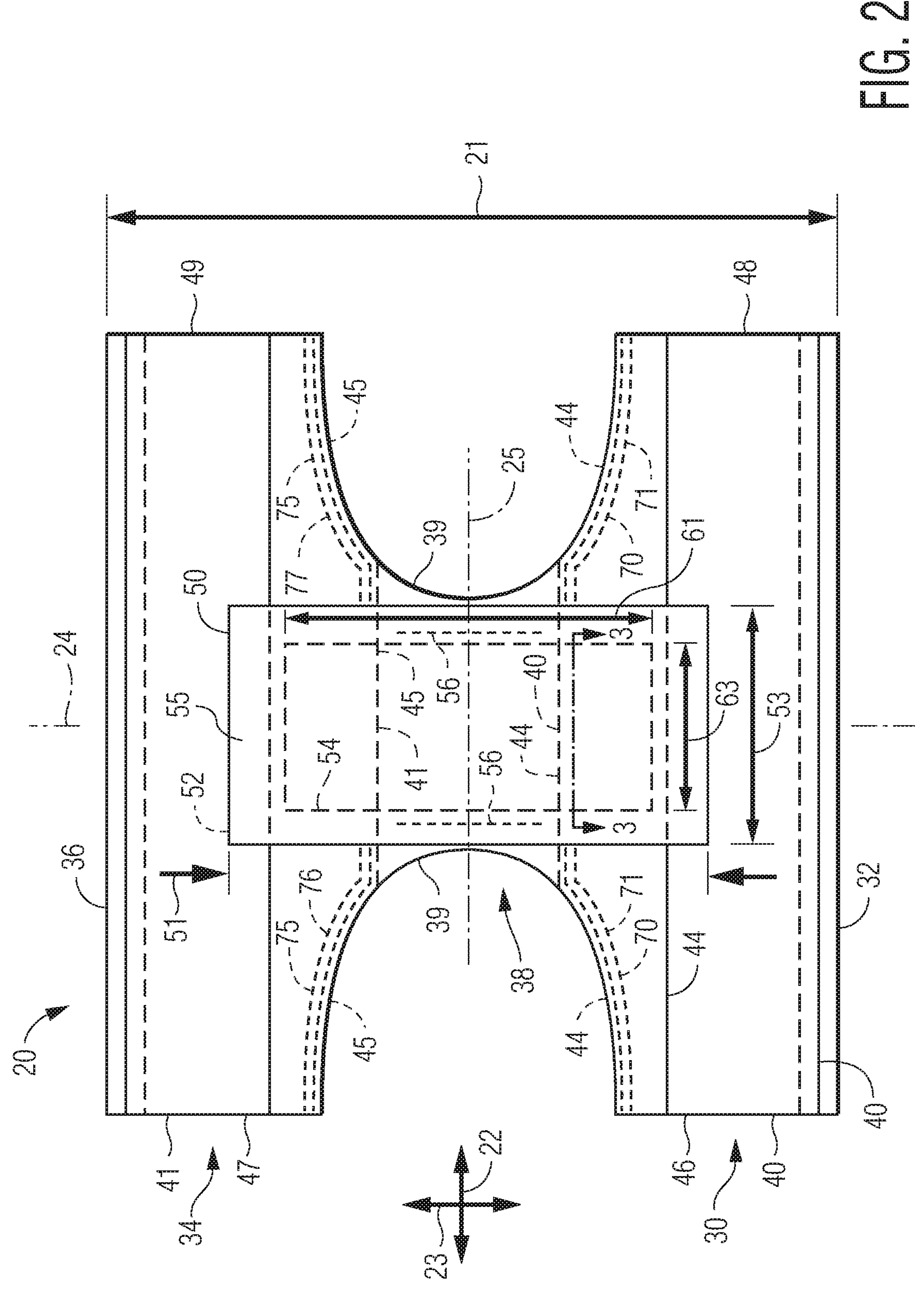
FIG. 2 is a plan view of the absorbent article of FIG. 1 in an open and laid flat configuration.

Referring to FIGS. 1-2, a garment 20 extends along a longitudinal direction 23 and a lateral direction 22 perpendicular to the longitudinal direction 23. As used in describing the various embodiments of the garment 20, according to aspects of the present disclosure, the terms "longitudinal" and "lateral" have their customary meaning, as indicated by the central longitudinal axis 24 and the central lateral axis 25. The central longitudinal axis 24 lies in the plane of the garment when the garment is in a fully stretched and laid-flat condition, while the front and rear panels are separated, and is generally parallel to a vertical plane that bisects a standing wearer into left and right body halves when the garment is worn. The central lateral axis 25 lies in the plane of the garment and is generally perpendicular to the central longitudinal axis 24. The garment 20 has a front region 30 defining a front waist end edge 32, a rear region 34 defining a rear waist end edge 36, and a crotch region 38 positioned longitudinally between the front region 30 and the rear region 34. The crotch region 38 defines two laterally opposed crotch side edges 39. The garment 20 defines a garment length 21 that extends from the front waist end edge 32 to the rear waist end edge 36.

The garment 20 includes a front panel 40 which defines a front panel leg edge 44 spaced longitudinally inward from the front waist end edge 32, and first and second laterally opposed front panel side edges 46, 48. The garment 20 also includes a rear panel 41 which defines a rear panel leg edge 45 spaced longitudinally inward from the rear waist end edge 36, and first and second laterally opposed rear panel side edges 47, 49. "Longitudinally inward (or inboard)" as used to describe garment embodiments herein means in a direction longitudinally toward the central lateral axis 25. Likewise, "laterally inward (or inboard)" as used to describe garment embodiments herein means in a direction laterally toward the central longitudinal axis 24. The front panel 40 is longitudinally spaced apart from the rear panel 41. The front and rear panels 40 generally comprise elasticized materials so as to conform to a wearer's body.

A pair of side seams 84, 84 connects the front region 30 to the rear region 34, such that the garment 20 defines a waist opening 27 and a pair of leg openings 28. The side seams can be permanent but tearable, such as by way of adhesive, thermal, pressure, or ultrasonic bonding, or can be more readily releasable as well as refastenable, such as via the use of mechanical fastening elements.

The garment 20 may further include at least one front leg elastic member 70 disposed adjacent the front panel leg edge 44, and/or at least one rear leg elastic member 75 disposed adjacent the rear panel leg edge 45. Such leg elastic members 70 and/or 75 help to provide additional elastic support around the leg openings 28 to enhance the fit and leakage protection of the garment 20. Each leg elastic member 70, 75 can comprise a single ribbon, strand, or thread (or the like) of elastic material, or each can comprise two, three, or more ribbons, strands, or threads (or the like) of elastic material. In particular embodiments, the rear leg elastic member 75 and/or the front leg elastic member 70 extends laterally across the entire garment width. In other embodiments, such as that representatively illustrated in FIGS. 1 and 2, the rear leg elastic member 75 can comprise a pair of rear leg elastic members, such as first and second rear leg elastic members 76, 77 positioned on opposite sides of the absorbent composite 50. Similarly, the front leg elastic member 70 can comprise a pair of front leg elastic members, such as first and second front leg elastic members 71, 72 positioned on opposite sides of the absorbent composite 50. In preferred embodiments, such as that representatively illustrated in FIGS. 1 and 2, each rear leg elastic member 75 can comprise a plurality of elastomeric strands, and/or each front leg elastic member 70 can comprise a plurality of elastomeric strands.

In particular embodiments, an absorbent composite 50 is connected to and between the front panel 40 and the rear panel 41. The absorbent composite 50 may comprise a composite structure formed of a liquid impermeable barrier layer 52 defining a width 53 and a length 51, an absorbent body 54 (sometimes referred to as an absorbent core herein) comprising absorbent material, a liquid permeable liner 55, and/or crotch elastic members 56. As used herein, the term "absorbent material" may mean fibrous absorbent material, superabsorbent material (SAM), or a combination of both fibrous absorbent material and SAM. The absorbent body 54, in some embodiments, may comprise a layered structure that includes multiple regions of liquid-absorbing materials such as fibrous absorbent material and/or SAM. The absorbent body 54 defines a length 61 and a width 63. Further description of exemplary absorbent bodies 54 of the present disclosure is presented below with respect to FIG. 3.

It should be understood that the exemplary pant-like garment 20 is only one possible example of an absorbent garment which may be used with the described absorbent bodies 54 of the present disclosure. Such garments 20 as those shown in FIGS. 1 and 2 may be generally described as garments formed using a cross-machine direction (CD) manufacturing process. Alternative exemplary garments which may be used with the described absorbent bodies 54 may include those garments formed by a machine-direction (MD) manufacturing process. In general, the present disclosure is not meant to be limited to the specifically disclosed absorbent garments. Rather, the described absorbent bodies 54 may be used within any suitable chassis structure for retaining the described absorbent bodies 54 on a wearer. In even further contemplated embodiments, the described absorbent bodies 54 may not be used with any chassis structure at all. Rather, the absorbent bodies 54 may be constructed so as to be able to be placed directly in contact with a wearer's body—for example using body-adhesive disposed on a body-side surface of the absorbent bodies 54.

Figure 3:
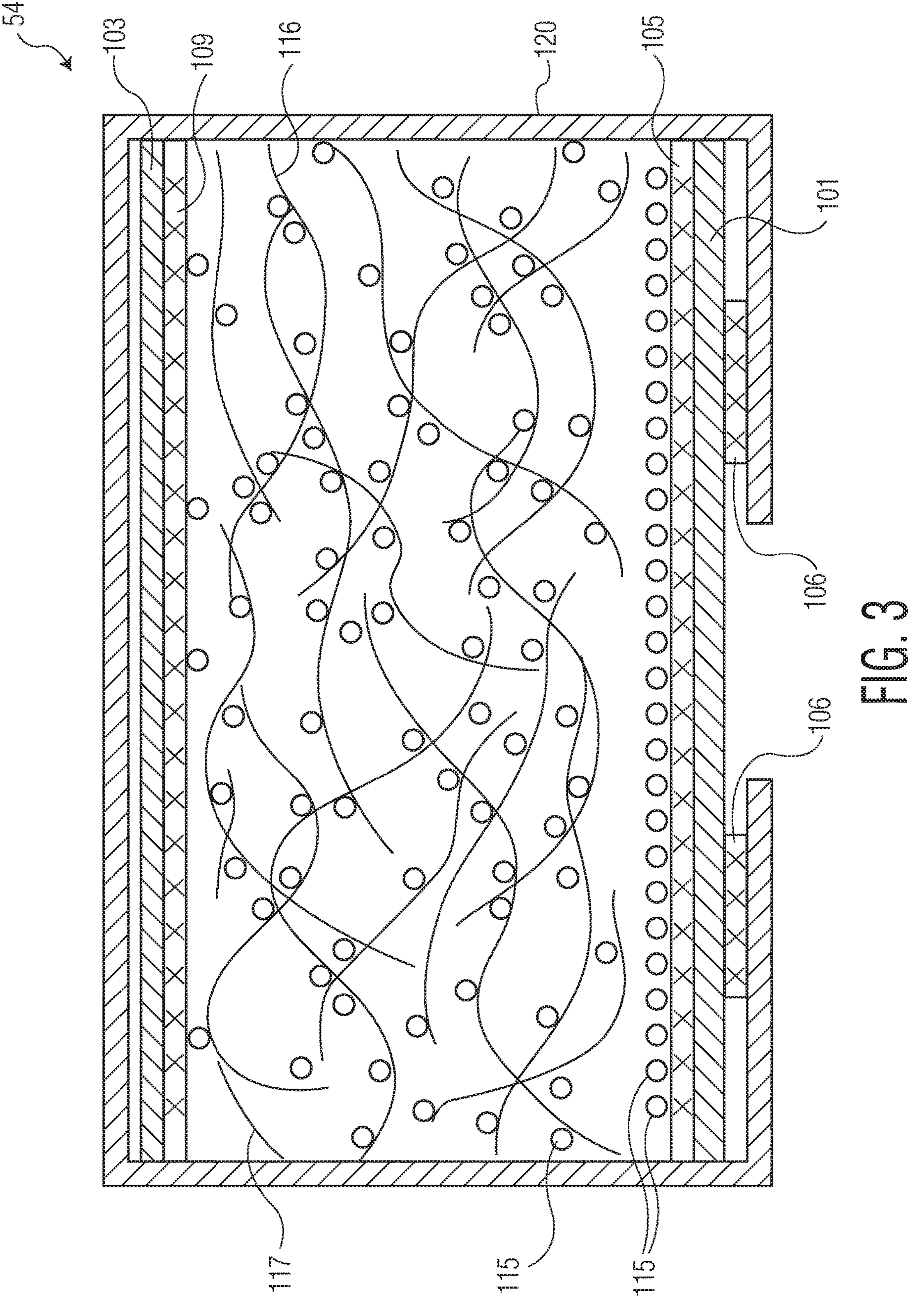
FIG. 3 is a cross-section of an exemplary absorbent body, according to aspects of the present disclosure.

FIG. 3 depicts an exemplary cross-section of the absorbent body 54 of FIG. 2, as viewed along line 3-3. In general, the absorbent body 54 of the present disclosure may comprise multiple different materials, with some of the materials layered together to form the body 54.

Describing the specific embodiment of the absorbent body 54 shown in FIG. 3, the exemplary absorbent body 54 comprises both a bottom covering material 101 and a top covering material 103 both of which are disposed about a reinforcing material 116. The absorbent body 54 may further comprise a corewrap material 120, which is optional in some embodiments.

The bottom covering material 101 and the top covering material 103 may be formed of any suitable materials. At least the top covering material 103 may be liquid permeable and may perform well in the uptake and wicking of fluid. In some embodiments, the bottom covering material 101 may also be liquid permeable and perform well in the uptake and wicking of fluid. Although, in other embodiments, the bottom covering material 101 may be liquid impermeable to help prevent liquid from leaking out of the body 54.

The covering materials 101 and/or 103 may include natural and synthetic fibers such as, but not limited to, polyester, polypropylene, acetate, nylon, polymeric materials, cellulosic materials and combinations thereof. In various embodiments, the fluid transfer layer 84 can be hydrophilic. In various embodiments, the covering materials 101 and/or 103 can be hydrophobic and can be treated in any manner known in the art to be made hydrophilic. A few exemplary suitable materials comprise tissue materials, spunbond and/or meltblown materials (e.g. spunbond-meltblown materials and spunbond-meltblown-spunbond materials), spunlace materials, HYDROKNIT® materials, which are a class of materials commercially available from Kimberly-Clark World Wide, Inc., airlaid materials, through-air bonded carded webs (TABCW), and coform materials. The covering materials 101, 103 may have basis weights ranging from between about 5 grams per square meter (gsm) and about 55 gsm. According to some specific embodiments of the present disclosure, the top covering material 103 may be a tissue, SMS, or spunbond material having a basis weight of between about 7 gsm and about 20 gsm. In other embodiments, the top covering material 103 may be a coform, spunlace, or airlaid material having a basis weight of between about 35 gsm and about 55 gsm. According to other specific embodiments of the present disclosure, the bottom covering material 101 may be a coform, spunlace, airlaid, or Hydroknit® material having a basis weight between about 30 gsm and about 50 gsm. Although, these are just some examples. Other suitable materials and/or materials having basis weights different than the above identified ranges may be used in other embodiments.

The reinforcing material 116 may help to provide some structural integrity to the body 54 and to assist in liquid uptake and distribution. Another benefit of the reinforcing material 116 is that it may help to stabilize absorbent material within the absorbent body 54, for example absorbent material embedded within the reinforcing material 116. In general, the reinforcing material 116 may comprise a non-woven material comprised of multiple individual fibers 117. For example, the reinforcing material 116 may be a spunbond material or a spunbond-meltblown-spunbond (SMS) material. In other embodiments, the nonwoven material may be a porous nonwoven material such as a TABCW or a chemically bonded nonwoven material or the like. In some specific embodiments, the reinforcing material 116 may be comprised substantially of polyolefin bi-component fibers, or polyolefin mixed bi-component and eccentric fibers, or just polyolefin eccentric fibers. Although, it should be understood that these are just some exemplary materials. Other suitable materials may be used in other contemplated embodiments. The basis weight of the reinforcing material 116 may preferably be between about 30 gsm and about 60 gsm, or between about 35 gsm and about 55 gsm, or between about 40 gsm and about 50 gsm in other embodiments.

The corewrap material 120 may wrap at least partially around the top covering material 103, the reinforcing material 116, and the bottom covering material 101. As shown in FIG. 3, the corewrap material 120 may wrap partially around the materials 101, 103 and the reinforcing material 116 leaving a gap between ends of the corewrap material 120 in what is sometimes called a "C-fold" configuration. Although the gap between ends of the corewrap material 120 is shown adjacent the bottom covering material 101, in other embodiments the gap may be located adjacent the top covering material 103. In other embodiments, however, the corewrap material 120 may wrap fully around the materials 101, 103 and the reinforcing material 116 such that the materials 101, 103 and the reinforcing material 116 are fully enclosed by the corewrap material 120.

The corewrap material 120 may be bonded to one of the materials 101, 103 through adhesive seam beads 106. Such adhesive beads 106 may extend along a length dimension of the absorbent body 54 and be disposed adjacent to ends of the corewrap material 120. Although, in other embodiments, different adhesive configurations may be used to bond the corewrap material 120 to the materials 101, 103 and/or the reinforcing material 116. For example, instead of just adhesive beads 106, adhesive may cover a majority of a side of the corewrap material 120 which faces the materials 101, 103 and the reinforcing material 116 such that the corewrap material 120 is bonded to the to the materials 101, 103 and the reinforcing material 116 all the way around the structure. In still further embodiments, additional adhesive beads may be employed such that the corewrap material 120 is bonded to both of the materials 101, 103. In general, the corewrap material 120 may be bonded to the materials 101, 103 and/or the reinforcing material 116 in any suitable fashion.

The corewrap material 120 may be comprised of a tissue material, spunbond and/or meltblown material (e.g. spunbond-meltblown material or spunbond-meltblown-spunbond material), spunlace material, HYDROKNIT® material, which are a class of materials commercially available from Kimberly-Clark World Wide, Inc., airlaid material, through-air bonded carded web (TABCW), and coform material. The corewrap material 120 may have a basis weight of between about 8 gsm and about 35 gsm. Although, it should be understood these are only exemplary materials and basis weights. In general, any suitable material at any suitable basis weight may be used.

As mentioned previously, the corewrap material 120 is optional in some embodiments. In some of these optional embodiments, the top covering material 103 may be bonded directly to the bottom covering material 101, such as by adhesive seam-beads 106, thereby enclosing the reinforcing material 116 without use of a corewrap material 120. Although, it should be understood that other adhesive configurations may be used to bond the materials 101, 103 together in these embodiments.

In at least some of these embodiments which do not include the corewrap material 120, the top covering material 103 may wrap around the reinforcing material 116 to bond with the bottom covering material 101. In other embodiments, both of the bottom covering material 101 and the top covering material 103 may wrap partially around the reinforcing material 116, or the bottom covering material 101 may wrap around the majority of the reinforcing material 116 to bond with the top covering material 103. The bottom covering material 101 or the top covering material 103 may wrap around the reinforcing material 116 and at least a portion of the other of the bottom covering material 101 and the top covering material 103 such that at least a portion of the other of the bottom covering material 101 and the top covering material 103 is enclosed. In such a configuration, the material 101 or 103 which wraps may form a C-fold or may fully enclose the other of the material 101, 103. In still other embodiments, the body 54 may only comprise a single covering material 101 or 103. In such embodiments, the single covering material 101 or 103 may wrap around the reinforcing material 116 and be bonded to itself fully enclosing the reinforcing material 116.

The absorbent body 54 may also contain absorbent material to provide the absorbent body 54 with beneficial fluid intake and storage (e.g. fluid retention) qualities. For example, the absorbent body 54 may comprise SAM disposed throughout the body 54, as depicted by SAM particles 115 in FIGS. 3, 7, 8, and 10. In some embodiments, the absorbent material of body 54 may include absorbent material comprised of substantially only SAM or may comprise both SAM and fibrous absorbent material (such as pulp fluff) in other embodiments. In the present disclosure, the phrase "substantially only" means that the qualified material may comprise greater than or equal to 90% of the total weight of the described material of the absorbent body 54. For example, where the absorbent body 54 includes absorbent material comprising substantially only SAM, the body 54 then comprises an amount of SAM weighing greater than or equal to 90% of the total weight of all of the absorbent material of body 54.

In order to maintain the absorbent body 54 as a cohesive structure, and to assist in stabilizing the absorbent material within the body 54, the body 54 may further comprise adhesive. In general, the adhesive may be applied to different materials of the body 54 so as to form different adhesive layers, such as adhesive layers 105, 109. Adhesive layer 105 may be applied to either the bottom covering material 101 and/or the reinforcing material 116 in order to laminate the bottom covering material 101 to the reinforcing material 116. Likewise, the adhesive layer 109 may be applied to the top covering material 103 and/or the reinforcing material 116 to laminate the top covering material 103 to the reinforcing material 116.

Figure 4:
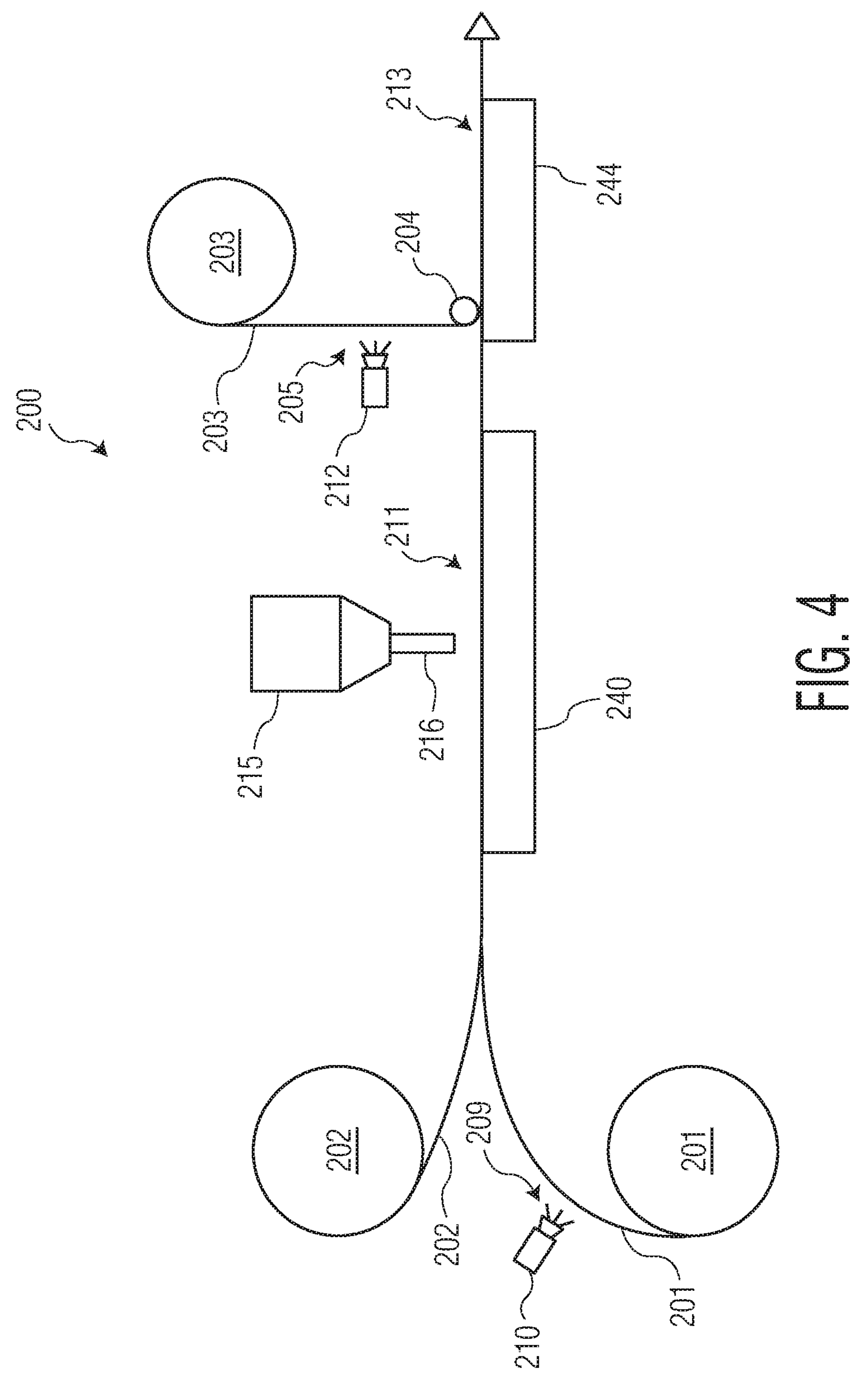
FIG. 4 is a schematic depiction of an exemplary method for forming absorbent bodies of the present disclosure.

FIG. 4 is a schematic depiction of a method 200 of manufacturing the absorbent bodies 54 of the present disclosure. In a first step, a first covering material 201 having a top side and a bottom side may be unwound from a spool comprising material forming the first covering material 201. The first covering material 201 may correspond to the top covering material 103 described previously with respect to the absorbent bodies 54 of the present disclosure. Although, in other embodiments, the first covering material 201 may correspond to the bottom covering material 101 described previously. A first adhesive 209 may be applied to the top side of the first covering material 201 by adhesive applicator 210 forming a first adhesive layer on the first covering material 201. The adhesive 209 forming the first adhesive layer may correspond to the adhesive layer 109 described previously. Although, in other embodiments, the adhesive 209 forming the first adhesive layer may correspond to the adhesive layer 205 described previously.

As shown, a reinforcing material 202 having a top side and a bottom side may also be unwound from a spool and may further be coupled to the first covering material 201, with the adhesive 209 sandwiched between the top side of the first covering material 201 and the bottom side of the reinforcing material 202. The reinforcing material 202 may correspond to the reinforcing material 116 described above. Although shown as being applied to the top side of the first covering material 201 in FIG. 4, in alternative embodiments, the adhesive 209 may be applied to the bottom side of the reinforcing material 202. Accordingly the adhesive 209 may operate to laminate the top side of the first covering material 201 directly to the bottom side of the reinforcing material 202. As described herein, the descriptor of "directly" means that two materials are bonded together without intervening materials (other than a bonding material, such as an adhesive). Accordingly, the top side of the first covering material 201 may be considered bonded directly to the bottom side of the reinforcing material 116 through adhesive 209.

The adhesive 209 may be applied at an add-on rate of between about 0.5 gsm and about 10 gsm. In other preferred embodiments, the adhesive 209 may be applied at an add-on rate of between about 1 gsm and about 5 gsm. The adhesive 209 can be applied according to any conventional adhesive application method, such as blowing, spraying, slot-coating, or the like. Additionally, any suitable patterning may be used, including swirl patterns, bead patterns, lines, or the like.

Next, the combined first covering material 201 and reinforcing material 202 are transported to a conveyer 240. While the first covering material 201 and the reinforcing material 202 are disposed over the conveyer 240, SAM (such as SAM particles 115 shown in FIG. 3) may be dispensed onto the reinforcing material 202. For example, the SAM may be stored in a hopper 215 and may be dispensed through conduit 216 to the reinforcing material 202. In some embodiments, the hopper 215 and conduit 216 may represent a gravity-feed system whereby the SAM is dispensed from the conduit 216 through gravity.

The SAM is dispensed from conduit 216 in a metered fashion such that a designated amount of SAM is deposited onto the reinforcing material 202. The SAM may be dispensed in such a fashion so as to achieve an add-on rate of between about 90 gsm to about 350 gsm. As the SAM contacts the reinforcing material 202, at least some of the SAM may penetrate into the reinforcing material 202. For example, the properties of the reinforcing material 202 may be such that voids between the fibers of the reinforcing material 202 are larger than at least some individual particles of the dispensed SAM, such that at least some particles of the dispensed SAM may filter into an interior of the reinforcing material 202, at least due to gravity.

In some embodiments, conveyer 240 could be a vacuum conveyer through which air is drawn through the first covering material 201 and the reinforcing material 202 and into the vacuum conveyer 240. In additional or alternative embodiments, the conveyer 240 may vibrate so as to vibrate the first covering material 201 and the reinforcing material 202 as the SAM is dispensed from the hopper 215. This addition of vacuum or vibration energy to the first covering material 201 and the reinforcing material 202 may help to increase the penetration of the dispensed SAM throughout the reinforcing material 202. However, in the embodiments disclosed herein, the use of vacuum and/or vibration energy has not been needed to achieve the described quantities of SAM stabilized within the reinforcing material 202. Although, in at least some embodiments, conveyer 240 is not necessary to the SAM dispensing process.

Next, a second covering material 203 may be unwound from a spool and brought to cover the partial core assembly 211 comprising the first covering material 201, the reinforcing material 202, and the applied SAM. In some embodiments, the second covering material 203 may be guided by guide roll 204. The second covering material 203 may correspond to the bottom covering material 101 in some embodiments, or the top covering material 103 in other embodiments.

An adhesive 205 may be applied by adhesive applicator 212 to the bottom side of the second covering material 203 before the second covering material 203 is brought to the partial core assembly 211. This second adhesive 205 may form an adhesive layer which may correspond to the adhesive layer 105. Although, in other embodiments, the adhesive 205 may form an adhesive layer which may correspond to the adhesive layer 109. As can be seen, the second adhesive 205 is applied to the bottom side of the second covering material 203 such that the second adhesive 205 is disposed between the bottom side of the second covering material 203 and the partial core assembly 211 and bonds the bottom side of the second covering material 203 directly to the partial core assembly 211. In practice, this results in a direct bond between the bottom side of the second covering material 203 and the top side of the reinforcing material 202. However, in other embodiments, the second adhesive 205 may be applied directly to the partial core assembly 211 before the second covering material 203 is applied to the partial core assembly 211. For instance, the second adhesive 205 may be applied directly to the top side of the reinforcing material 202 and the applied SAM deposited onto the reinforcing material 202.

The adhesive 205 may be applied at an add-on rate of between about 0.5 gsm and about 10 gsm. In other preferred embodiments, the adhesive 205 may be applied at an add-on rate of between about 1 gsm and about 5 gsm. The adhesive 205 can be applied according to any conventional adhesive application method, such as blowing, spraying, slot-coating, or the like. Additionally, any suitable patterning may be used, including swirl patterns, bead patterns, lines, or the like.

The core assembly 213, comprising the first covering material 201, the reinforcing material 202, the SAM, and the second covering material 203 (along with the adhesive 209 and 205) may then be processed further. For example, the core assembly 213 may be transferred to further processing stations by conveyer 244. In some embodiments, the core assembly 213 may be passed through a nip, imparting pressure and/or heat to the core assembly 213. Additionally or alternatively, the core assembly 213 may pass through a bonding station to seal the side edges of the core assembly 213. In still further embodiments, the core assembly may be passed to a corewrap station where a corewrap material, such as corewrap material 120, is wrapped at least partially around the core assembly 213. At least some of these embodiments may result in forming adhesive beads 106, as shown in FIG. 3.

The core assembly 213 may further be incorporated into an absorbent garment or an absorbent article pre-curser product. For example, the process 200 may be a sub-process of an absorbent garment formation process resulting in a finished absorbent garment product, such as article 20 shown in FIGS. 1 and 2. In such cases, the core assembly 213 may be cut into individual absorbent bodies 54 for incorporation into an absorbent garment or garment pre-curser product. Many such processes are well known in the art. In further embodiments, after the core assembly 213 has been formed, the core assembly 213 may be rolled. Such rolls of the core assembly 213 may then be transported for use in a separate absorbent garment manufacturing process.

In at least some embodiments, the core assembly 213 may be inverted prior to application into an absorbent garment or absorbent garment pre-curser product. For example, at least some of the embodiments of the process 200 as described with respect to FIG. 4 produce an absorbent body 54 by building the absorbent body 54 in an "upside down" fashion. That is, in some embodiments the first covering material 201, which is disposed on the bottom throughout the process 200, becomes the top covering material 103 of the absorbent body 54 when the body 54 is inverted. This "inverted" structure can be correspondingly seen in FIG. 3, where the bottom side of the top covering material 103 is bonded directly to the top side of the reinforcing material 116 by the adhesive layer 109, and where the bottom side of the reinforcing material 116 is bonded directly to the top side of the bottom covering material 101.

In building the absorbent body 54 in this fashion, the SAM is applied to what becomes the bottom side (e.g. the garment-facing side) of the reinforcing material 202 when the body 54 is placed into a product. In these embodiments, much of the SAM applied to the reinforcing material 202 stays at or close to the interface between the second covering material 203 and the reinforcing material 202, while some of the SAM penetrates into the reinforcing material 202.

When positioned into an absorbent article with the first covering material 201 becoming the top covering material 103 (e.g. the portion of the absorbent body 54 which is closest to a body-facing surface of such an article), the absorbent body 54 demonstrates beneficial performance over other absorbent bodies. Because the SAM has been applied to what becomes the bottom side of the reinforcing material 116, and because most of the SAM does not penetrate through the reinforcing material 116 so as to migrate to the top covering material 103, a relatively small amount of SAM is located proximate the top covering material 103. This structure provides for beneficial performance of the absorbent body 54 as it relates to intake speed and dryness, as will be described in more detail below.

Using the above described process, it has been found that control over stabilizing desired amounts of SAM within different locations of the absorbent body 54 may be achieved. In particular, it has been found that ensuring more than about 30% and less than about 85% of the total amount of SAM particles 115 within the body 54 are stabilized within the reinforcing material 116 (according to the SAM Stabilization Location Test Method) results in beneficial performance of the absorbent body 54. In other preferred embodiments, the amount of SAM particles 115 stabilized within the reinforcing material 116 may be between about 40% and about 75% of the total amount of SAM particles 115 within the body 54.

As used herein, the term 'stabilized' means retained. For example, as the SAM particles 115 contact the adhesive layer 105, the SAM particles 115 will become stuck to the adhesive layer 105 and become retained. Due to porosity of the reinforcing material 116, at least some of the SAM particles 115 are able to penetrate within the interior of the reinforcing material 116. These SAM particles 115 may filter through the pores in the reinforcing material 116 and ultimately become stuck somewhere within the reinforcing material 116—for example due to the size and/or shape and/or orientation of the fibers 117 and pores within the reinforcing material 116 and the size and shape of the SAM particles 115. Accordingly, these 'stuck' SAM particles 115 are retained within the reinforcing material 116 and considered stabilized within the reinforcing material 116. A determination about how much SAM is stabilized within different portions of the absorbent body 54 may be determined by the SAM Stabilization Location Test Method described herein.

If the amount of SAM particles 115 stabilized within the reinforcing material 116 is greater than about 85% of the total quantity of SAM particles 115 within the body 54, it has been found that gel-blocking can occur within the reinforcing material 116. Gel-blocking occurs due to the swelling action by the SAM particles 115 (due to fluid absorption) blocking access to other of the SAM particles 115 by fluid within and flowing through the reinforcing material 116. The swelling can lengthen a flow path of fluid within the reinforcing material 116, thereby negatively affecting (e.g. increasing) liquid intake speeds, rewet performance, and even retention capacity of the body 54 as compared to other bodies 54 with lower amounts of SAM particles 115 stabilized within the reinforcing material 116. Comparative results from a 3-insult liquid intake test indicates that an absorbent body according to absorbent body 54 where 40% of the total quantity of SAM particles 115 are stabilized within the reinforcing material 116 performed about 12% better than an absorbent body according to absorbent body 54 where 85% of the total quantity of SAM particles 115 are stabilized within the reinforcing material 116.

Accordingly, it is hypothesized that by having larger proportions of the SAM particles 115 stabilized within the reinforcing material 116, such as greater than about 85%, such particles 115 are swelling and blocking paths for the liquid to penetrate into the reinforcing material 116, thereby increasing intake speed to undesirable levels. In other embodiments, it may be preferable to have no more than about 70% of the total quantity of SAM particles 115 within the body 54 stabilized within the reinforcing material 116 in order to produce desirable liquid intake speeds.

On the other end, it has been found that if the amount of SAM particles 115 stabilized within the reinforcing material 116 is less than about 30% of the total quantity of SAM particles 115 within the body 54, a lamination strength between the reinforcing material 116 and the bottom covering material 101 can be negatively impacted. For example, with such a low percentage of the SAM particles 115 stabilized within the reinforcing material 116, a correspondingly high amount of SAM particles 115 are stabilized at the adhesive layer 105. The high amount of SAM particles 115 bonded to the adhesive layer 105 does not leave as much open adhesive of the adhesive layer 105 to bond with the reinforcing material 116 as in other embodiments where the amount of SAM particles 115 stabilized at the adhesive layer 105 is lesser. The lower bond strength between the reinforcing material 116 and the bottom covering material 101 can result in a lower pad integrity, which can impact the performance of the body 54 as well as comfort for a user.

With such a low percentage of the SAM particles 115 stabilized within the reinforcing material 116, it has also been found that SAM 'islands' can form on the adhesive layer 105. Such SAM 'islands' can be the result of there being too many SAM particles 115 to bond to the adhesive layer 105. As a result, the SAM particles 115 can migrate at the interface between the reinforcing material 116 and the bottom covering material 101, ultimately forming clumps or 'islands'. These SAM 'islands' can negatively affect the liquid uptake and retention capacity of the body 54, as well as cause uncomfortable lumps within the body 54.

Accordingly, due to the above mentioned issues, if is preferred that more than about 30% and less than about 85% of the total amount of SAM particles 115 within the body 54 are stabilized within the reinforcing material 116. This range is particularly useful when the amount of SAM particles 115 within the absorbent body is between about 90 gsm and about 350 gsm. Other preferred embodiments may have more than about 40% and less than about 75% of the total amount of SAM particles 115 within the body 54 stabilized within the reinforcing material 116 (as determined by the SAM Stabilization Location Test Method) where the total amount of SAM particles 115 within the absorbent body is between about 90 gsm and about 350 gsm.

In some particular embodiments, at least some of the SAM particles 115 may filter all the way through the reinforcing material 202 during the process 200. These SAM particles 115 then become stabilized by the adhesive 209, corresponding to the adhesive layer 109 as depicted in FIG. 3. However, SAM particles 115 stabilized in this manner generally comprise only a small fraction of the SAM particle 115 content of the absorbent body 54 resulting from the process 200. In general, it is desired that the amount of SAM particles 115 stabilized by the adhesive layer 109 is relatively low to ensure desired liquid intake speeds are achieved by the absorbent body 54. Swelling of the SAM particles 115 stabilized by the adhesive layer 109 will generally lengthen the fluid flow path into and through the body 54 and thereby generally cause a longer liquid intake time of the body 54, relative to absorbent bodies 54 having lower percentages of SAM particles 115 stabilized at the adhesive layer 109.

It has been found that a useful range for an amount of SAM particles 115 stabilized by the adhesive layer 109 which still results in an acceptable liquid intake speed (time) is less than about 10%, by weight, of the total amount of SAM particles 115 in the absorbent body 54, as determined according to the SAM Stabilization Location Test Method. In other embodiments, it may be preferred that less than about 7.5%, or less than about 5%, or less than about 2.5%, or less than about 1%, or less than about 0.5% of the total SAM particles 115 of the absorbent body 54 are stabilized at the adhesive layer 109, as determined according to the SAM Stabilization Location Test Method.

It has been further found that these particular stabilization percentages are useful where the reinforcing material 116 has particular properties. For example, the absorbent body 54 may perform well related to intake speed and dryness performance where the reinforcing material 116 is between about 25 gsm and about 80 gsm and where the SAM particles 115 are disposed within the absorbent body 54 at an amount between about 90 gsm and about 350 gsm. In other preferred embodiments, the reinforcing material 116 may be between 35 gsm and about 70 gsm, or between about 40 gsm and about 65 gsm, and where the SAM particles 115 are disposed within the absorbent body 54 at an amount between about 90 gsm and about 350 gsm.

It may additionally be beneficial for the reinforcing material 116 to have a thickness of between about 0.8 mm and about 3.0 mm according to the Reinforcing Material Height After Cutting Test Method, detailed below. In other preferred embodiments, the reinforcing material 116 may have a thickness, according to the Reinforcing Material Height After Cutting Test Method, of between about 1.0 mm and about 2.5 mm. This combination of basis weight and thickness allows for sufficient porosity of the reinforcing material 116 to allow for the desired SAM stabilization percentages detailed herein. For example, these ranges create a porosity of the reinforcing material 116 which allow the SAM particles 115 to penetrate into the reinforcing material 116 along with providing sufficient volume of the reinforcing material 116 for the SAM particles 115 to penetrate to result in the desired stabilization percentages.

If the reinforcing material 116 has a height that is greater than about 3.0 mm (according to the Reinforcing Material Height After Cutting Test Method) and has a basis weight of between about 25 gsm and about 80 gsm (depending on the specific type of material of the reinforcing material 116), the fiber-to-fiber spacing is such that it may not be possible to stabilize a desired amount of SAM particles 115 within the reinforcing material 116 because of the relatively large pores within the reinforcing material 116 caused by the great height and low basis weight. In other embodiments, it may not be possible to stabilize a desired amount of SAM particles 115 within the reinforcing material 116 where the reinforcing material 116 has a height greater than about 2.5 mm (according to the Reinforcing Material Height After Cutting Test Method) while having a basis weight of between about 20 gsm and 60 gsm (depending on the specific type of material of the reinforcing material 116).

Conversely, where the reinforcing material 116 has a height less than about 0.8 mm or about 1.0 mm (at any suitable basis weight, e.g. between about 15 gsm and about 150 gsm), the reinforcing material 116 may not have enough thickness to hold and stabilize a desired amount of SAM particles 115 within the reinforcing material 116. In such examples, the lower amount of SAM particles 115 stabilized within the reinforcing material 116 leaves a relatively higher amount of SAM particles 115 located at the interface between the reinforcing material 116 and the bottom covering layer 101 which can cause issues with SAM islands and/or lamination strength as described above. In determining these issues with high and low reinforcing material 116 heights at the described basis weights, it should be understood that these issues were found when using amounts of SAM particles 115 required to achieve a presence of between about 90 gsm and about 350 gsm, which generally represents useful amounts of SAM particles in absorbent articles.

Figure 5:
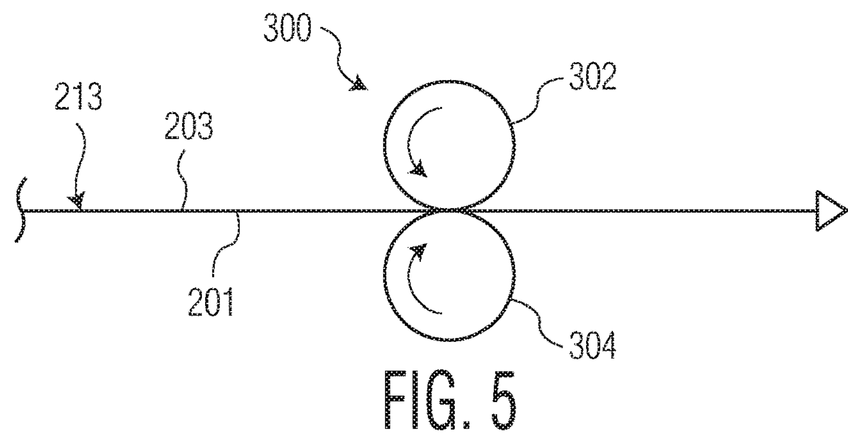
FIG. 5 is a schematic depiction of an exemplary method for embossing absorbent bodies of the present disclosure.

Referring back to the process 200 of FIG. 4, it was described that once the core assembly 213 has been formed, additional processing steps may be performed. One optional additional processing step not described previously is embossing of the core assembly 213. FIG. 5 depicts an exemplary embossing process 300 which may be used to emboss the core assembly 213. It should be understood that although the process 300 may impart beneficial properties onto the core assembly 213 (and thus absorbent bodies 54 formed from the core assembly 213), this embossing process is a purely optional step in the process for forming the absorbent bodies 54.

As can be seen in FIG. 5, the core assembly 213 may be advanced to embossing rolls 302, 304 which form a nip. In at least some embodiments, the core assembly 213 may be advanced to the embossing rolls 302, 304 with the second covering material 203 oriented upward so as to contact the embossing roll 302 and the first covering material 201 oriented downward so as to contact the embossing roll 304. As the core assembly 213 advances between the embossing rolls 302, 304, the embossing rolls 302, 304 operate to emboss the core assembly 213. Preferably, the embossing roll 302 comprises embossing elements 342 which press into the core assembly 213. In the orientation described above, the embossing elements 342 may press into the second covering material 203 as the core assembly 213 advances between the embossing rolls 302, 304. In general, it may be most advantageous to emboss a side of the core assembly 213 to which the SAM particles 115 were applied.

It has been found that embossing the core assembly 213 by pressing or more embossing elements 342 into the second covering material 203 can help to increase the amount of SAM particles 115 stabilized within the reinforcing material 116 of the core assembly 213. Accordingly, embossing the core assembly 213, and particularly embossing the second covering material 203 of the core assembly 213, can help to achieve a desired percentage of SAM particles 115 stabilized within the reinforcing material 116. Of course, individual absorbent bodies 54 may be formed from a core assembly 213 prior to embossing of the core assembly 213, and these individual absorbent bodies 54 may be embossed individually and achieve the benefits detailed herein.

Figure 6A:
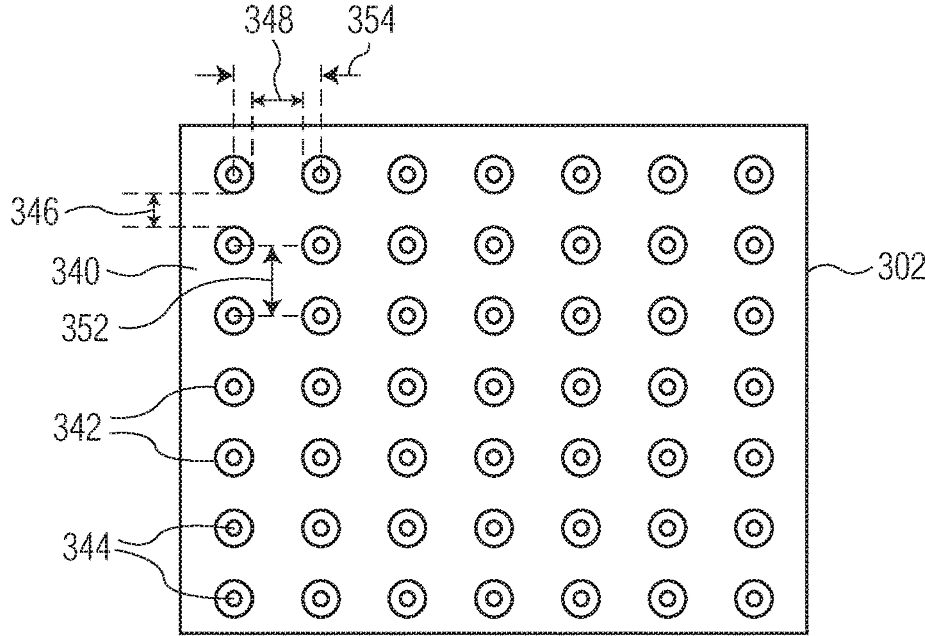
FIG. 6A is a top-plan view of a portion of an exemplary embossing surface that may be used with the embossing method of FIG. 5.
Figure 6B:
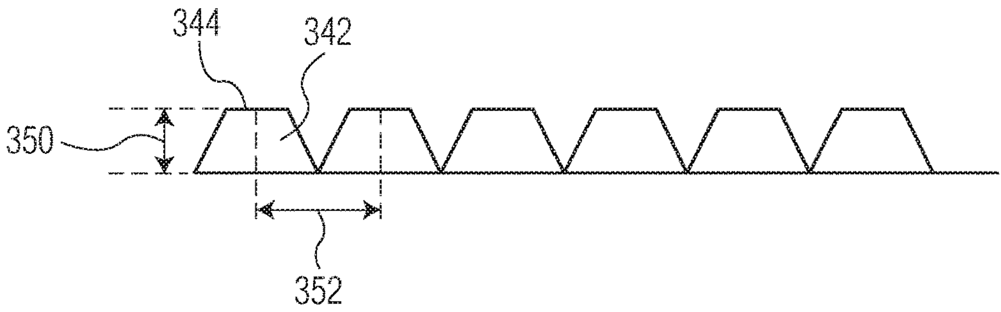
FIG. 6B is side view of a portion of an exemplary embossing surface that may be used with the embossing method of FIG. 5.

FIGS. 6A and 6B depict a top plan view and side plan view, respectively, of a portion of the face 340 of the embossing roll 302 (shown in a flat configuration). As can be seen, the face 340 of the embossing roll 302 may comprise a plurality of embossing elements 342 having embossing surfaces 344. In at least some embodiments, the embossing roll 304 may be a sooth roll. In some embodiments, the rolls 302 and/or 304 may be heated, but this is not necessary in all embodiments.

In general, the embossing elements 342 may have any suitable size and shape. In at least some embodiments, the embossing elements 342 are cone shaped with a flat embossing surface 344 (as shown in FIG. 6B). In other embodiments, the embossing elements 342 may be cylindrically-shaped and/or have a rounded embossing surface 344. In further embodiments, the embossing elements 342, and/or the embossing surfaces 344 themselves, may have an oval shape, or a rectangular shape, or a star shape, or any other suitable shape. In still further embodiments, the embossing elements 342 may form embossing bars which extend laterally, longitudinally, or diagonally across the face 340 of the roll 302.

The embossing elements 342 may have longitudinal spacing 346 and lateral spacing 348 between adjacent embossing elements 342. The embossing surfaces 344 of adjacent embossing elements 342 may have longitudinal spacing 352 and lateral spacing 354 (as measured from centers of the embossing surfaces 344). In some embodiments, the lateral and/or longitudinal spacings 346, 348 may be zero such that bases of the embossing elements 342 longitudinally and/or laterally abut each other, while achieving lateral and/or longitudinal spacing between the embossing surfaces 344 of such embossing elements 342 through tapering of the embossing elements 342 throughout their height 350, as shown in FIG. 6B.

The embossing elements 342 may be generally configured to impart an embossed area onto the core assembly 213 (or individual absorbent body 54) embossed by the process 300. The core assembly 213 or the individual absorbent bodies 54 may have a surface which faces the embossing elements 342 during the process 300, which becomes embossed. For example, a top surface of the second covering material 203 may be the surface of the core assembly 213 facing the embossing elements 342 during the process 300 in some of the embodiments described previously. This surface of the core assembly 213 or the individual absorbent bodies 54 which faces the embossing elements 342 during the process 300 has an area, which may be called a core assembly area or absorbent body area herein.

The embossed area of the core assembly 213 or the individual absorbent bodies 54 may be considered those portions of the surface of the core assembly 213 or the individual absorbent bodies 54 indented due to the embossing process 300. Areas of these indented portions may be added together and then divided by the core assembly or absorbent body area to obtain an embossed area percentage. As one simplistic example, if an area of a core assembly 213 or an individual absorbent body 54 is 100 square mm, and this core assembly or absorbent body area has been embossed by ten embossing elements 342 to produce indentations each having an area of 1 square mm, then the embossed area percentage of the core assembly 213 or the individual absorbent body 54 would be considered to be 10% (e.g. 10 square mm of embossing surfaces 344 divided by the 100 square mm area of the core assembly 213 or the individual absorbent body 54).

In one experiment, a series of absorbent bodies 54 were made according to the process 200. A first of these formed absorbent bodies 54 remained un-embossed and was determined to have approximately 37.2% of the SAM particles 115 within this first absorbent body 54 stabilized within its reinforcing material 116. A second of these formed absorbent bodies 54 was embossed, for example by a process such as process 300, to have an embossed area percentage of 8%. It was determined that this second absorbent body 54 had approximately 40.5% of the SAM particles 115 within this second absorbent body 54 stabilized within its reinforcing material 116. A third of these formed absorbent bodies 54 was embossed, for example by a process such as process 300, to have an embossed area percentage of 12%. It was determined that this third absorbent body 54 had approximately 48.9% of the SAM particles 115 within this third absorbent body 54 stabilized within its reinforcing material 116.

Accordingly, the experiment showed that embossing such core assemblies 213 in the manner described with respect to process 300 can increase the amount of SAM particles 115 embedded within the reinforcing materials 116 of the core assemblies 213 (and, thus, absorbent bodies 54 formed from such embossed core assemblies 213) by between about 0.98% and about 1.06% per percent of embossed area. Therefore, it may be beneficial to emboss the core assemblies 213 of the present disclosure to achieve an embossed area percentage of the assemblies 213 of between greater than about 0% and about 42%. This range of embossing areas may achieve sufficient SAM particle 115 penetration into the reinforcing materials 116 to allow the formation of absorbent bodies 54 having the previously disclosed percentages of SAM particles 115 stabilized within the reinforcing materials 116.

Other preferred ranges of embossed area percentages of the core assemblies 213 of the present disclosure may be between about 5% and about 35%, or between about 10% and about 30%, or between about 10% and about 25%, or between about 10% and about 20%. These smaller ranges may be more broadly useful for achieving a desired percentage of stabilized SAM particles 115 within reinforcing materials 116 of core assemblies 213 of the present disclosure. For example, employing an embossing apparatus (e.g. comprising at least embossing rolls 302, 304) configured to achieve an embossed area percentage of the core assemblies 213 of between about 10% and about 20% may be more effective at producing core assemblies 213 having a desired percentage of SAM particles 115 (for instance, between about 30% and about 85%) stabilized within the reinforcing materials 116 of the core assemblies 213 for core assemblies 213 with a broader range of differences (e.g. reinforcing material type, basis weight, and thickness, and SAM add-on amounts, etc.) than an embossing apparatus configured to achieve an embossed area percentage of between about 0-10% or between about 20-42%. This disclosure should not be construed to limit the disclosed useful range of embossed area percentages of about 0% and about 42%, but rather construed to understand a benefit of using an embossing assembly configured to achieve and embossed area percentage of between about 10% and 20%—such as not needing to change or adjust the embossing apparatus (so as to achieve a different embossed area percentage to ensure a desired percentage of the SAM particles 115 are stabilized within the reinforcing material 116) when changing properties of the core assemblies 213, such as a composition, basis weight, or height of the reinforcing material 116, or the add-on amount of SAM particles 115 within the core assemblies 213.

Referring back to the embossing pin heights 350, the embossing pin heights 350 may generally vary between about 0.5 mm and about 4.0 mm when used in accordance with the structures (e.g. core assemblies 213 and absorbent bodies 54) and materials (reinforcing material 116, covering materials 101, 103, 201, 203) disclosed herein. In general, it may be preferred that a combination of pin height 350 and nip spacing between the rolls 302, 304 does not produce too great of an embossing depth. The embossing depth may be considered the distance which the elements 342 penetrate into the core assembly 213 or the individual absorbent body 54. If the combination of pin heights 350 and nip spacing produces too great of an embossing depth, the SAM particles 115 may be pushed through the reinforcing material 116 all the way to, and stabilized at, the first covering material 201 (or the top covering material 103), for example by the adhesive 210/109). Accordingly, this may reduce the percentage of the SAM particles 115 stabilized within the reinforcing material 116 to a lower than desired level and/or increase the percentage of SAM particles 115 stabilized at the material 201/103 to an undesired level.

It has been found that it may be preferred for the embossing depth to be less than about 90% of the thickness of the core assembly 213 or the individual absorbent body 54. In other embodiments, it may be preferred that the embossing depth is less than about 85%, or less than about 80%, or less than about 75%, or less than about 70% of the thickness of the core assembly 213 or the individual absorbent body 54. On the other end, if the embossing depth is not deep enough, the effectiveness of increasing the percentage of SAM particles 115 stabilized within the reinforcing material 116 may be reduced. Accordingly, it may be preferred that the embossing depth is greater than about 25% of the thickness of the core assembly 213 or the individual absorbent body 54. In other preferred embodiments, it may be preferred that embossing depth is greater than about 30%, or greater than about 35%, or greater than about 40%, or greater than about 45%, or greater than about 50% of the thickness of the core assembly 213 or the individual absorbent body 54.

As described above and with respect FIG. 5, the process 300 is shown being performed on a core assembly 213. However, in other embodiments, the process 300 may be performed on partial core assemblies 211. For example, during the process 200, after the SAM particles have been dispensed onto the reinforcing material 116 (for example from hopper 215 and through conduit 216), the partial core assembly 211 comprising the first covering material 201, the reinforcing material 202, and the dispensed SAM particles (and possibly adhesive 209), can be advanced through process 300. In such embodiments, the embossing elements 342 may emboss the reinforcing material 202 by contacting the reinforcing material 202 directly. In contrast, with respect to the process 300 depicted in FIG. 5, the embossing elements 342 may directly contact the second covering material 203 and emboss both the second covering material 203 and the reinforcing material 202 simultaneously—for instance because the embossing depth is such that the embossing elements 342 penetrate at least to some extent into the reinforcing material 202.

Another effect that embossing the core assemblies 213 (and/or absorbent bodies 54) of the present disclosure has aside from increasing the amount of SAM particles 115 stabilized within the reinforcing materials 116 of the assemblies 113 or bodies 54, is that the embossing localizes at least some of the SAM particles 115 within the reinforcing materials 116. This feature can be seen more clearly with respect to FIGS. 7 and 8 which are photographs of reinforcing materials 116 taken out of different absorbent bodies 54. The reinforcing material 116 shown in the photograph of FIG. 7 was taken from an absorbent body 54 which was not embossed while the reinforcing material 116 shown in the photograph of FIG. 8 was taken from an absorbent body 54 which was embossed.

Figure 7:
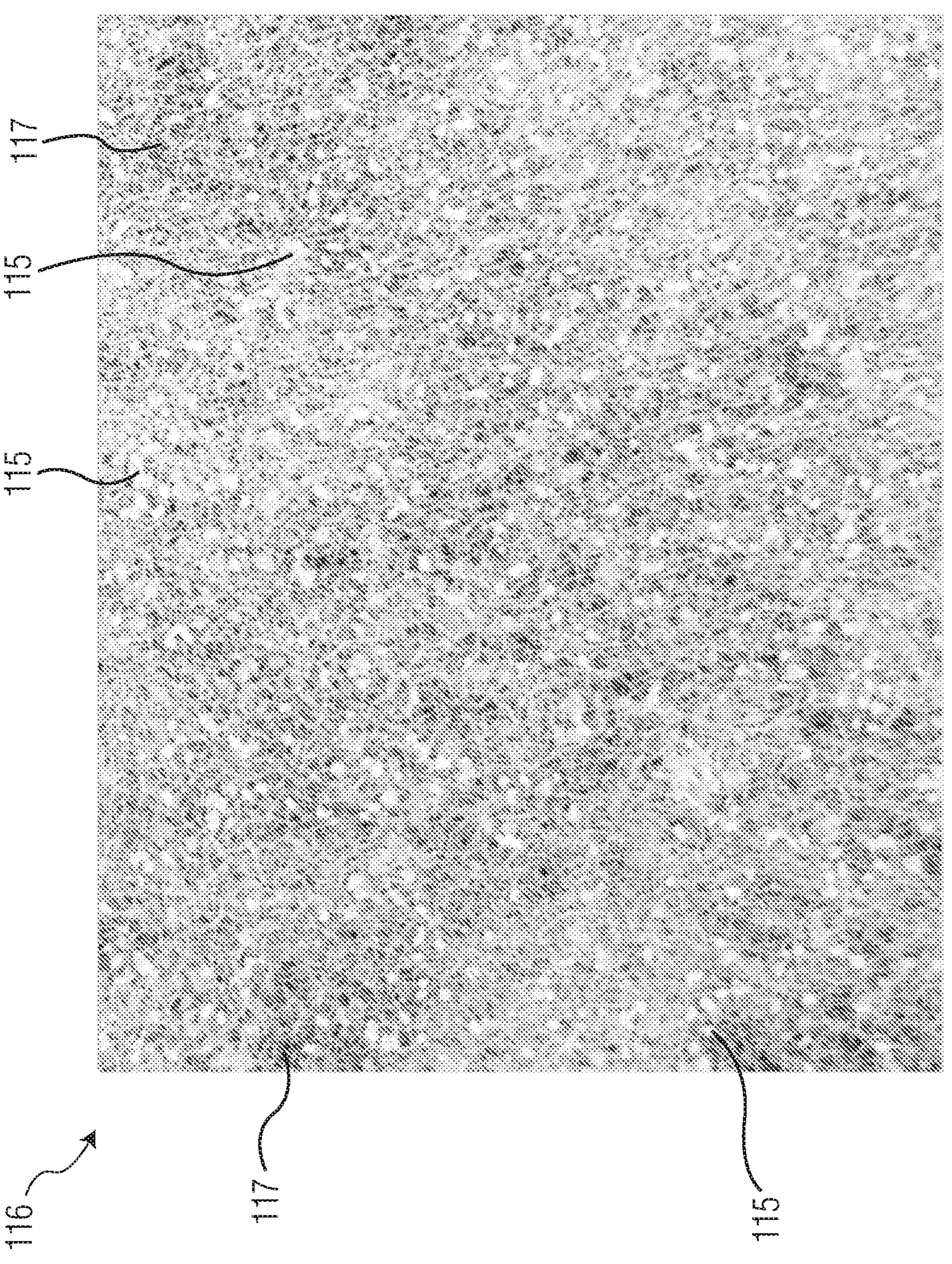
FIG. 7 is a photograph of an un-embossed reinforcing material containing superabsorbent particles, according to aspects of the present disclosure.
Figure 8:
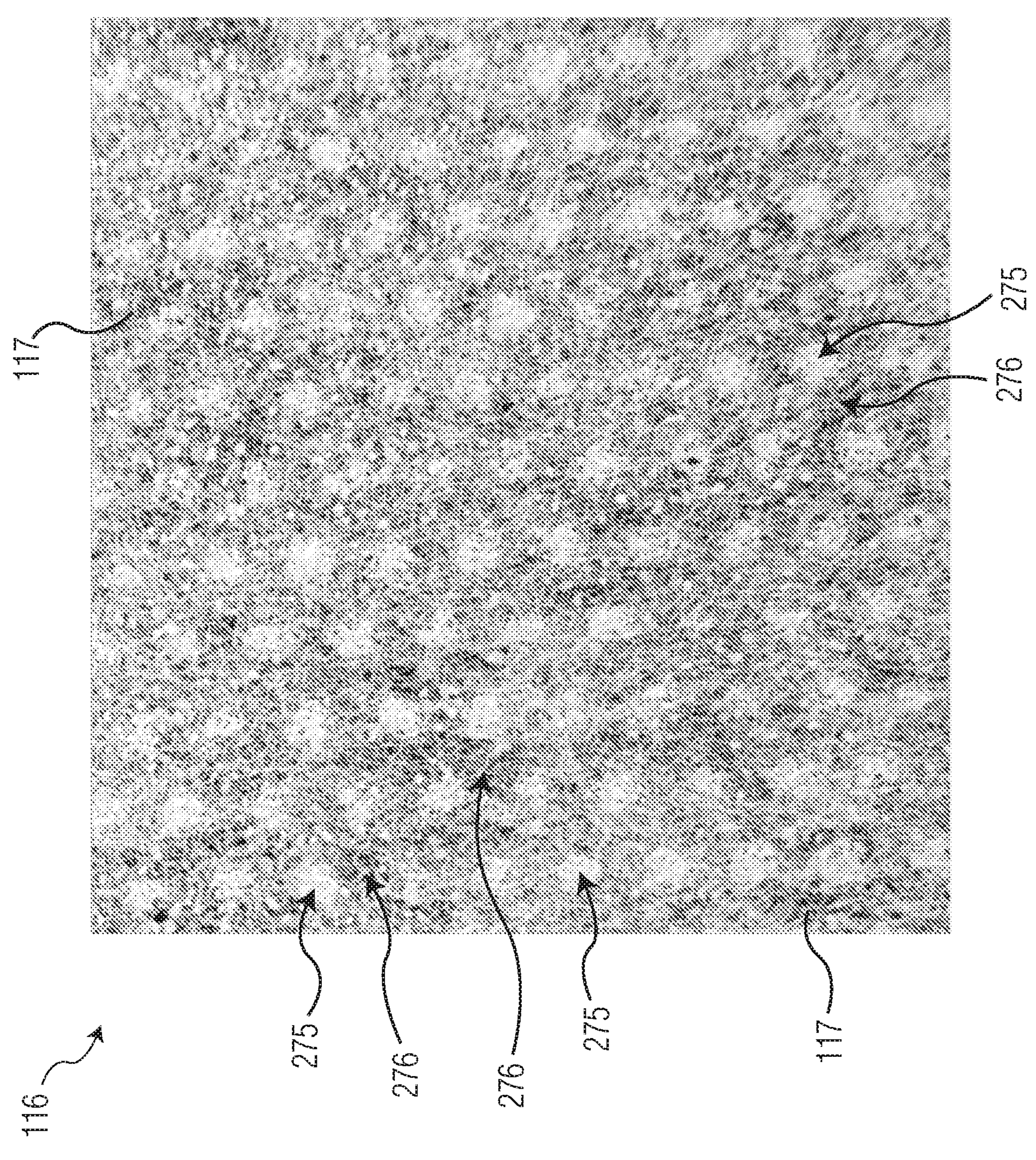
FIG. 8 is a photograph of an embossed reinforcing material containing superabsorbent particles, according to aspects of the present disclosure.

The FIGS. 7 and 8 depicting the different reinforcing materials 116 show both individual SAM particles 115 and individual fibers 117 in each of the reinforcing materials 116 of the FIGS. 7 and 8. The SAM particles 115 of the reinforcing material 116 of FIG. 7 can be seen to be more or less randomly distributed through the reinforcing material 116, thereby producing a relatively uniform distribution of SAM particles 115 throughout the reinforcing material 116. There are not any areas within the reinforcing material 116 of FIG. 7 which have substantially higher concentrations of SAM particles 115 than other areas of the reinforcing material 116. Or, to the extent that there are differences in SAM particle 115 concentrations on a micro-scale, such differences are oriented randomly throughout the reinforcing material 116 of FIG. 7.

Conversely, the reinforcing material 116 of FIG. 8 can be seen to have high-SAM particle concentration regions 275 and low-SAM particle concentration regions 276. These regions 275, 276 of high and low SAM particle concentrations are formed according to a pattern. That is, these regions 275, 276 of high and low SAM particle concentrations do not occur randomly. Instead, these regions 275, 276 of high and low SAM particle concentrations are oriented in a regular, repeating sequence. In the particular example of FIG. 8, the regions 275 are surrounded by the regions 276. Although, it should be understood that other patterns may be formed. For example, the regions 275 may form longitudinally or laterally extending, alternating, bars or strips, with regions 276 oriented on both sides of a single region 275. In still further embodiments, the regions 275 may be offset (longitudinally and or laterally) with respect to adjacent regions 275 instead of aligned as is shown in FIG. 8. In general, such patterns of locations of regions 275 may correspond substantially to the embossing pattern used to emboss a core assembly 213 or absorbent body 54. Accordingly, the locations of regions 275 may correspond to embossed areas of the reinforcing material 116.

Embossing core assemblies 213 and/or absorbent bodies 54 of the present disclosure to achieve such patterned regions of high and low SAM particle concentrations can provide a benefit beyond the previously described embossing benefit of increasing the amount of SAM particles 115 stabilized within the reinforcing material 116. By forming regions 275, 276 of high and low SAM concentrations, fluid is more easily able to flow through the reinforcing material 116 than when the SAM is more evenly distributed throughout the reinforcing material 116. For example, in the embodiment of FIG. 7 where the SAM particles 115 are more uniformly distributed throughout the reinforcing material 116, as fluid flows into and permeates through the reinforcing material 116, the SAM particles 115 stabilized within the reinforcing material 116 will begin to absorb the fluid and swell. This swelling can close off paths for the fluid to flow, thereby increasing path lengths by which the fluid is able to flow all the way through the reinforcing material 116. However, in the embodiment of FIG. 8, as the SAM particles 115 swell, the regions of low SAM concentration 276 may remain relatively open and un-blocked to better allow fluid to continue to flow all the way through the reinforcing material 116. This can result in the absorbent body 54 performing better with respect to intake performance than un-embossed bodies 54.

Figure 9:
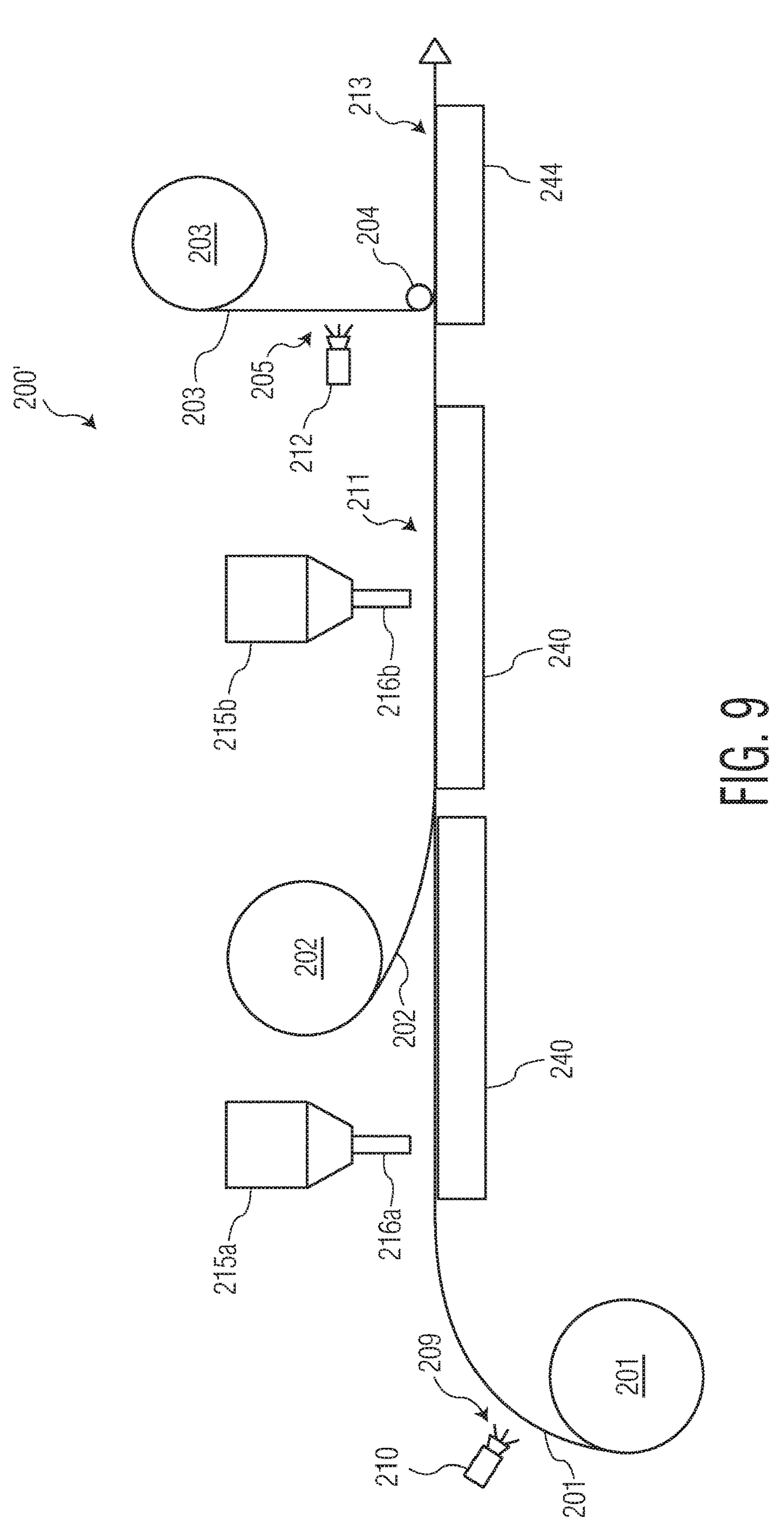
FIG. 9 is a schematic depiction of an exemplary method for forming absorbent bodies of the present disclosure.

Accordingly, embossing of the absorbent bodies 54 in the manner described herein may be useful with respect to further absorbent body structures than just those absorbent bodies 54 disclosed with respect to FIG. 3. FIG. 9 is a schematic drawing of an exemplary manufacturing process 200' for producing further absorbent bodies which may be embossed according to process 300 to achieve at least some of the benefits described herein. The process 200' is similar to the process 200, except that the process 200' has two separate SAM dispensing steps. In the process 200', SAM particles (such as SAM particles 115) may be dispensed directly onto the first covering material 201 (or onto adhesive 209 which was disposed on the first covering material 201), for example from SAM hopper 215*a* and through conduit 216*a*. After the SAM particles have been dispensed onto the first covering material 201, the reinforcing material 202 may be brought together with the first covering material 201, as in the process 200. Next, additional SAM particles may be dispensed onto the reinforcing material 202, for example from SAM hopper 215*b* and through conduit 216*b*, in a similar fashion to that described above with respect to process 200. The rest of the steps of process 200' are similar to those described with respect to process 200, for example combining the second covering material 203 with the partial core assembly 211 to form the core assembly 213.

The resulting core assemblies 213 of the process 200' may then have a much higher percentage (of the total amount of SAM particles 115 in the core assemblies 213 of process 200') of SAM particles 115 stabilized at the first covering material 201 than the percentages described with respect to core assemblies 213 produced by the process 200. These core assemblies 213 made by the process 200' can be processed in any similar fashion to that described with respect the core assemblies 213 produced by the process 200, such as by being separated into individual absorbent bodies and placed into absorbent garments or garment pre-cursor products, such as shown in FIGS. 1 and 2. In at least some embodiments, this additional processing may include embossing these core assemblies 213 made by the process 200' according to the process 300 described herein.

Figure 10:
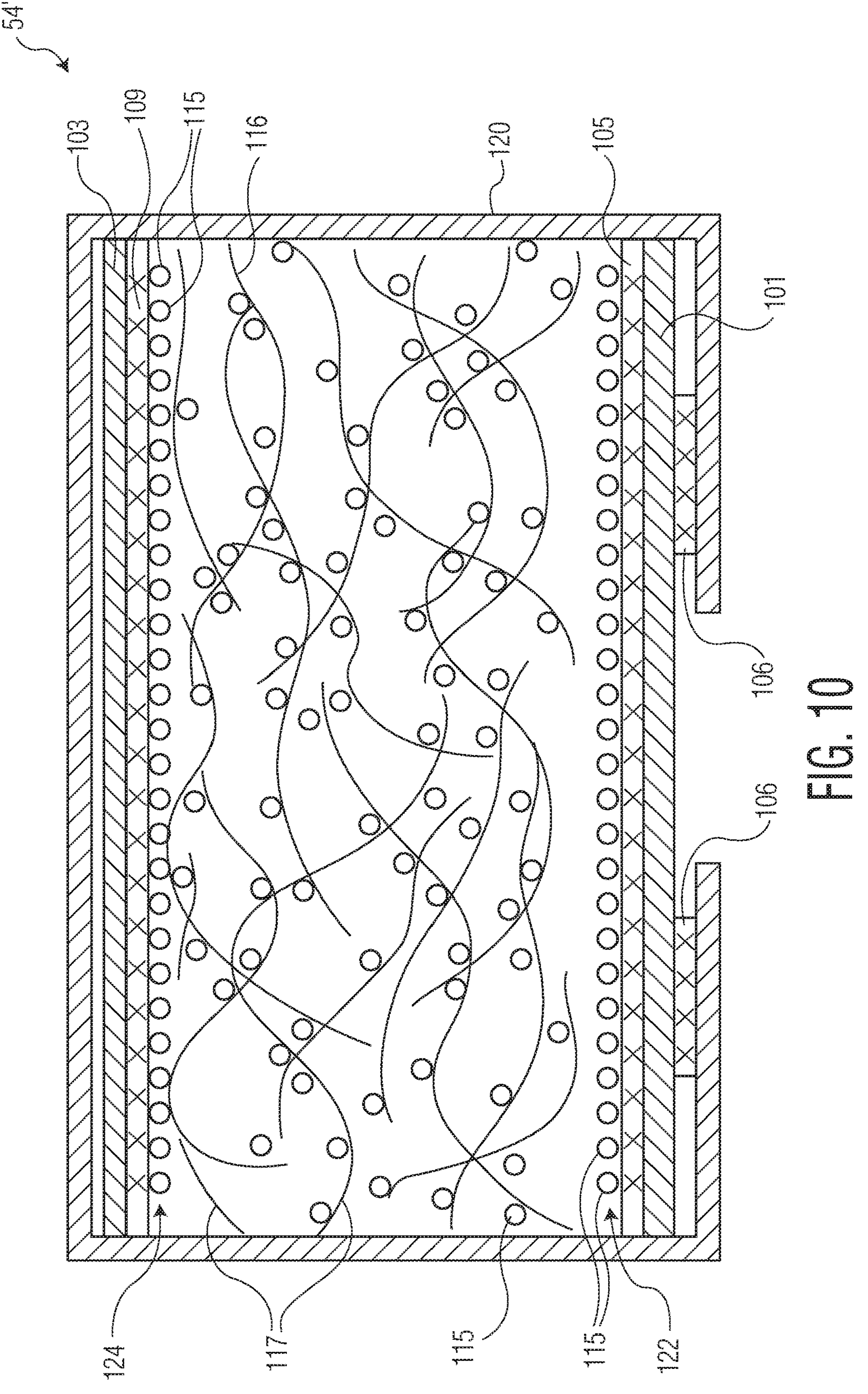
FIG. 10 is a cross-section of an exemplary absorbent body, according to aspects of the present disclosure.

FIG. 10 depicts an exemplary cross-section, as viewed along line 3-3 of FIG. 2, where the absorbent body 54 of FIG. 2 is an absorbent body formed from the process 200'. The absorbent body of FIG. 10 is labeled as absorbent body 54'. As can be seen, there are many more SAM particles 115 stabilized at the top covering material 103 than as shown in the absorbent body 54. The absorbent body 54' may sometimes be called a 5-layer complex absorbent body (or core) in the art.

Such absorbent bodies 54' may also benefit from the embossing process 300 described with respect to FIG. 5, as do the absorbent bodies 54 described with respect to FIG. 3. For example, performing the embossing of core assemblies 213 formed by the process 200' (or directly on individual absorbent bodies 54') may help to further distribute SAM particles 115 from away from the bottom covering material 203 to become stabilized within the reinforcing material 116. Additionally, the embossing may help to localize the SAM particles 115 within the reinforcing material 116 of the absorbent body 54' to help create regions of low-SAM concentration for better fluid flow and permeation through the reinforcing material 116 of the absorbent body 54'.

SAM Stabilization Location Test Method:

In order to determine the amount of SAM particles 115 stabilized in the different portions of an absorbent body, such as absorbent body 54, the following steps may be performed.

First, a table may be formed detailing the basis weights of the different materials comprising the absorbent body. These basis weights can be determined according to an absorbent body product specification used in forming such an absorbent body, or may be determined according to various known analytical techniques.

Table 1 lists exemplary components of an absorbent body according to absorbent body 54 described herein on the left-hand side of Table 1. The basis weights of the various components in the absorbent body are listed in the second column. Adding up the basis weights of each of the absorbent body components may result in a total basis weight value, listed at the bottom of the second column. Next, a ratio may be calculated and recorded (in the third column) for each absorbent body component, comparing the basis weight of each component to the total basis weight value.

TABLE 1

| | Basis Weight (gsm) | Ratio | Total Weight (g) |
|---|---|---|---|
| Bottom Corewrap Material (e.g. material 101) | 50 | 13.2% | 4.62 |
| Bottom-side Adhesive Layer (e.g. adhesive layer 105) | 5 | 1.3% | 0.455 |
| SAM | 240 | 63.5% | 22.2 |
| Reinforcing Material (e.g. material 116) | 40 | 10.6% | 3.71 |
| Top-side Adhesive Layer (e.g. adhesive layer 109) | 2.5 | 0.7% | 0.245 |
| Top Corewrap Material (e.g. material 103) | 40 | 10.6% | 3.71 |
| Total | 378 | 100% | 35 |

The absorbent body may be carefully cut into a 100 mm by 100 mm specimen, using sharp scissors or another suitable cutting instrument. The specimen is then placed with the bottom corewrap material facing upward on an empty tray. The specimen is then weighed, in grams, on a scientific scale having an accuracy to at least hundredths of a gram. This total specimen weight is recorded in grams to the nearest hundredth gram. To help ensure clarity around this test method, a total specimen weight of 35.00 grams will be used for illustration and calculation purposes.

The total weight of each of the components of the absorbent core may then be calculated using the determined ratios recorded in Table 1. For example, knowing that the bottom corewrap material contributes 13% to the total weight of the absorbent body, it can be determined that the bottom corewrap material weighs approximately 4.62 grams for a total specimen weight of 35.00 grams. Similar total weight values can be calculated for each of the components and recorded in Table 1.

Next, Electrolube Freezer Spray (FRE400) should be sprayed onto the bottom corewrap material. While holding down the reinforcing material and the top corewrap material, the bottom corewrap material is steadily and carefully peeled away from the reinforcing material. The bottom corewrap material is placed in an empty tray. The rest of the specimen (e.g. the reinforcing material and the top corewrap material) is carefully picked up and positioned over the try containing the bottom corewrap material. The combined reinforcing material and the top corewrap material are then carefully turned over so that the reinforcing material is facing downward, and the combined material is shaken side-to-side six (6) times so that any residual SAM not stabilized in the reinforcing material falls out and into the tray containing the bottom corewrap material. During the shaking, the combined material should move laterally about 1 inch before its direction is reversed, and the shaking should take about two (2) seconds.

With the bottom corewrap material still in the tray, in addition to any residual SAM shaken out of the combined reinforcing material and top corewrap material, a weight is recorded in grams to the nearest hundredth gram ("Measured Weight 1").

The reinforcing material and the top corewrap material are then placed in an empty tray with the top corewrap material facing upward. Electrolube Freezer Spray (FRE400) should then be sprayed onto the top corewrap material. While holding down the reinforcing material, the top corewrap material is steadily and carefully peeled away from the reinforcing material. With the reinforcing material still in the tray, a weight is recorded, in grams, to the nearest hundredth gram ("Measured Weight 2").

Finally, calculations can be performed to determine a percentage of the SAM particles of the absorbent body stabilized within or to the various components of the absorbent body. To determine the percentage of the SAM particles stabilized to the bottom corewrap material (e.g. the amount of SAM particles stabilized by the adhesive layer 105), the following calculation may be performed. The determined weight of the bottom-side adhesive layer (e.g. 0.245 g in the ongoing example) and the determined weight of the top corewrap material (e.g. 3.71 g in the ongoing example) may be subtracted from the Measured Weight 1. Since the Measured Weight 1 consists of the weight of the bottom corewrap material of the specimen, the bottom adhesive layer adhered to the bottom corewrap material, SAM particles stabilized by the bottom adhesive layer and residual SAM particles not stabilized within the reinforcing material (which were shook out off of the reinforcing material), the resulting value is the weight, in grams, of the SAM particles weighed while obtaining the Measured Weight 1 value. This resulting value can then be divided by the determined total weight of the SAM particles in the specimen (e.g. 22.2 g in the ongoing example) to arrive at a percentage of SAM stabilized at the bottom corewrap material in the specimen.

To determine the percentage of the SAM particles stabilized within the reinforcing material, the following calculation may be performed. The determined weight of the reinforcing material (e.g. 3.71 g in the ongoing example) may be subtracted from the Measured Weight 2 value. Since the Measured Weight 2 value included only the reinforcing material, including the SAM particles stabilized within the reinforcing material, the resulting calculation returns the total weight of the SAM particles stabilized within the reinforcing material. This total weight of the SAM particles stabilized within the reinforcing material may then be divided by the determined total weight of the SAM particles in the specimen (e.g. 22.2 g in the ongoing example) to arrive at a percentage of SAM stabilized in the reinforcing material in the specimen.

Finally, to determine the percentage of SAM particles stabilized at the top corewrap material, the determined total weight of SAM particles stabilized at the bottom corewrap material and the determined total weight of SAM particles stabilized within the reinforcing material may be subtracted from the determined total weight of the SAM particles in the specimen (e.g. 22.2 g in the ongoing example). This resulting calculated weight of the SAM particles stabilized at the top corewrap material may then be divided by the determined total weight of the SAM particles in the specimen to arrive at the percentage of SAM particles stabilized at the top corewrap material.

Reinforcing Material Height after Cutting Test Method:

The material to be measured may be raw material procured directly from a manufacturer prior to application into a product or obtained from a product of which the material is a component. Where the material needs to be cut to fit the testing apparatus, the material should be cut to a size not less than 90 mm by 102 mm (3.5 by 4 inches). If the material is cut prior to testing, the material should be allowed to rest for at least twenty minutes prior to performing the testing. The testing conditions may align with ASTM E 171-187, Standard Atmospheres for Conditioning and Testing Materials, 1994.

The testing apparatus may be a STARRET® bulk tester, and the testing may be performed under a controlled loading pressure of approximately 0.345 kPa (0.05 pound-force per square inch (psi)). The output data can be recorded to the nearest 0.01 mm. However, substantially equivalent equipment and settings may alternatively be employed. The STARRET® bulk tester should have a minimum line pressure of 4.2 kg/cm$^2$ (60 psi) and should not exceed 4.55 kg/cm$^2$ (65 psi). The pressure coming from the foot pedal to the cylinder should be adjust to 207 kPa (30 psi). A 76.2 mm (3 inch) platen should be used. The descent speed should be adjusted to be 3 seconds plus or minus 0.5 second. Next, the indicator should be turned on and zeroed by pressing the ZERO button. Finally, the foot pedal should be depressed and the testing material should be placed onto the base, and the platen lowered by using the foot pedal. After 3 seconds, the displayed value should be read and recorded. This recorded value represents the desired height value of the tested material (sometimes called the material bulk or caliper).

Example Absorbent Bodies:

According to aspects of the present disclosure, particular embodiments of the absorbent body 54 have been found to be particularly advantageous. According to a first preferred embodiment, the absorbent body 54 may comprise a top covering material 103 formed of a tissue material, an SMS material, or a spunbond material having a basis weight of between about 7 gsm and about 20 gsm. A bottom covering material 101 of this first preferred embodiment may be formed of a coform or spunlace material having a basis weight of between about 30 gsm and about 40 gsm. The reinforcing material 116 of this first preferred embodiment may be comprised of a polyolefin bi-component fiber having a basis weight of between about 40 gsm and about 50 gsm. The SAM may be applied so as form an average basis weight of between about 195 gsm and about 225 gsm within the body 54 of this first preferred embodiment.

According to a second preferred embodiment, the absorbent body 54 may comprise a top covering material 103 formed of a tissue material, an SMS material, or a spunbond material having a basis weight of between about 7 gsm and about 20 gsm. A bottom covering material 101 of this second preferred embodiment may be formed of a coform, spunlace, or HYDROKNIT® material having a basis weight of between about 40 gsm and about 50 gsm. The reinforcing material 116 of this second preferred embodiment may be a polyolefin mixed bi-component and eccentric fiber material having a basis weight of between about 40 gsm and about 50 gsm. The SAM may be applied so as form an average basis weight of between about 205 gsm and about 240 gsm within the body 54 of this second preferred embodiment.

According to a third preferred embodiment, the absorbent body 54 may comprise a top covering material 103 formed of a tissue material, an SMS material, or a spunbond material having a basis weight of between about 7 gsm and about 20 gsm. A bottom covering material 101 of this third preferred embodiment may be formed of a coform, spunlace, or airlaid material having a basis weight of between about 40 gsm and about 50 gsm. The reinforcing material 116 of this third preferred embodiment may be a polyolefin mixed bi-component and eccentric fiber material having a basis weight of between about 40 gsm and about 50 gsm. The SAM may be applied so as form an average basis weight of between about 225 gsm and about 255 gsm within the body 54 of this third preferred embodiment.

According to a fourth preferred embodiment, the absorbent body 54 may comprise a top covering material 103 formed of a coform, spunlace, or airlaid material having a basis weight of between about 35 gsm and about 55 gsm. A bottom covering material 101 of this fourth preferred embodiment may be formed of a coform or spunlace material having a basis weight of between about 35 gsm and about 45 gsm. The reinforcing material 116 of this fourth preferred embodiment may be a polyolefin eccentric fiber material having a basis weight of between about 30 gsm and about 40 gsm. The SAM may be applied so as form an average basis weight of between about 100 gsm and about 130 gsm within the body 54 of this fourth preferred embodiment.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

EMBODIMENTS

Embodiment 1

A method of forming an absorbent body may comprise moving a first covering material in a machine direction, the first covering material having a top side and a bottom side, moving a reinforcing material in the machine direction and combining the reinforcing material with the first covering material, the reinforcing material having a top side and a bottom side, applying absorbent material comprising superabsorbent particles to the top side of the reinforcing material, moving a second covering material in the machine direction, the second covering material having a top side and a bottom side, and combining the second covering material with the first covering material and the reinforcing material to form a laminate structure of the first covering material, the reinforcing material, and the second covering material, with the first covering material disposed underneath the reinforcing material and the second covering material disposed on top of the reinforcing material, and embossing the laminate structure.

Embodiment 2

The method of embodiment 1, wherein embossing the laminate structure may comprise embossing a top side of the laminate structure.

Embodiment 3

The method of embodiment 1, wherein embossing the laminate structure may comprise embossing the second covering material.

Embodiment 4

The method of any of embodiments 1-3, further comprising applying adhesive to one of the top side of the first covering material and the bottom side of the reinforcing material, and applying adhesive to one of the top side of the reinforcing material and the bottom side of the second covering material.

Embodiment 5

The method of any of embodiments 1-4, wherein the laminate structure may comprise a laminate area, and wherein embossing the laminate structure may comprise forming an embossed area greater than about 0% of the laminate area and less than about 42% of the laminate area.

Embodiment 6

The method of any of embodiments 1-4, wherein the laminate structure may comprise a laminate area, and wherein embossing the laminate structure may comprise forming an embossed area greater than about 5% of the laminate area and less than about 35% of the laminate area.

Embodiment 7

The method of any of embodiments 1-4, wherein the laminate structure may comprise a laminate area, and wherein embossing the laminate structure may comprise forming an embossed area greater than about 10% of the laminate area and less than about 30% of the laminate area.

Embodiment 8

The method of any of embodiments 1-7, wherein the laminate structure may have a thickness, and wherein embossing the laminate structure may comprise embossing the laminate structure to a depth of less than about 90% of the laminate structure thickness.

Embodiment 9

The method of any of embodiments 1-7, wherein the laminate structure may have a thickness, and wherein embossing the laminate structure may comprise embossing the laminate structure to a depth of less than about 80% of the laminate structure thickness.

Embodiment 10

The method of any of embodiments 1-9, wherein the laminate structure may have a thickness, and wherein embossing the laminate structure may comprise embossing the laminate structure to a depth of greater than about 40% of the laminate structure thickness.

Embodiment 11

The method of any of embodiments 1-10, wherein embossing the laminate structure may comprise passing the laminate structure through an embossing nip formed by a first embossing roll and a second embossing roll, the first embossing roll comprising a plurality of embossing elements projecting from a surface of the first embossing roll where a height of the embossing elements is between about 0.8 mm and about 4.0 mm.

Embodiment 12

The method of any of embodiments 1-11, further comprising inverting the laminate structure.

Embodiment 13

The method of any of embodiments 1-12, further comprising coupling the absorbent body to an absorbent article chassis such that the first covering material forms a body-facing side of the absorbent body.

Embodiment 14

The method of any of embodiments 1-13, further comprising applying absorbent material comprising superabsorbent particles to the top side of the first covering material.

Embodiment 15

An absorbent body may comprise a top, liquid permeable covering material, a bottom covering material, a reinforcing material disposed between the top covering material and the bottom covering material, and superabsorbent material disposed within the reinforcing material in a pattern of high-SAM concentration regions and low-SAM concentration regions.

Embodiment 16

The absorbent body of embodiment 15, wherein the high-SAM concentration regions may be surrounded by low-SAM concentration regions.

Embodiment 17

The absorbent body of any of embodiments 15 and 16, wherein the high-SAM concentration regions and the low-SAM concentration regions may form alternating stripes within the reinforcing material.

Embodiment 18

The absorbent body of any of embodiments 15-17, wherein between about 30% and about 85%, by weight, of the total amount of superabsorbent material disposed between the top covering material and the bottom covering material may be stabilized within the reinforcing material, as determined according to the SAM Stabilization Location Test Method.

Embodiment 19

The absorbent body of any of embodiments 15-18, wherein less than about 10%, by weight, of the total amount of superabsorbent material disposed between the top covering material and the bottom covering material may be stabilized by the first adhesive layer, as determined according to the SAM Stabilization Location Test Method.

Embodiment 20

The absorbent body of any of embodiments 15-19, wherein the high-SAM concentration regions may correspond with embossed areas of the reinforcing material.

Embodiment 21

A method of forming an absorbent body may comprise moving a first covering material in a machine direction, the first covering material having a top side and a bottom side, moving a reinforcing material in the machine direction and combining the reinforcing material with the first covering material, the reinforcing material having a top side and a bottom side, applying absorbent material comprising superabsorbent particles to the top side of the reinforcing material, moving a second covering material in the machine direction and combining the second covering material with the first covering material and the reinforcing material to form a laminate structure of the first covering material, the reinforcing material, and the second covering material, with the first covering material disposed underneath the reinforcing material and the second covering material disposed on top of the reinforcing material, and embossing the reinforcing material.

Embodiment 22

The method of embodiment 21, wherein embossing the reinforcing material comprises embossing the reinforcing material prior to combining the second covering material with the first covering material and the reinforcing material to form a laminate structure of the first covering material, the reinforcing material, and the second covering material.

Embodiment 23

The method of any of embodiments 21 and 22, where embossing the reinforcing material comprises embossing the top side of the reinforcing material.

Embodiment 24

The method of any of embodiments 21-23, further comprising embossing the second covering material, wherein the embossing of the second covering material and the reinforcing material occurs simultaneously.

Embodiment 25

The method of any of embodiments 21-24, further comprising applying adhesive to one of the top side of the first covering material and the bottom side of the reinforcing material, and applying adhesive to one of the top side of the reinforcing material and the bottom side of the second covering material.

Embodiment 26

The method of any of embodiments 21-25, wherein the reinforcing material may comprise a reinforcing material area, and wherein embossing the reinforcing material may comprise forming an embossed area greater than about 0% of the reinforcing material and less than about 42% of the reinforcing material.

Embodiment 27

The method of any of embodiments 21-26, wherein the reinforcing material may comprise a reinforcing material area, and wherein embossing the reinforcing material may comprise forming an embossed area greater than about 5% of the reinforcing material area and less than about 35% of the reinforcing material area.

Embodiment 28

The method of any of embodiments 21-26, wherein the reinforcing material may comprise a reinforcing material area, and wherein embossing the reinforcing material may comprise forming an embossed area greater than about 10% of the reinforcing material area and less than about 30% of the reinforcing material area.

Embodiment 29

The method of any of embodiments 21-28, wherein the reinforcing material may have a thickness, and wherein embossing the reinforcing material may comprise embossing the reinforcing material to a depth of less than about 90% of the reinforcing material thickness.

Embodiment 30

The method of any of embodiments 21-28, wherein the reinforcing material may have a thickness, and wherein embossing the reinforcing material may comprise embossing the reinforcing material to a depth of less than about 80% of the reinforcing material thickness.

Embodiment 31

The method of any of embodiments 21-30, wherein the reinforcing material may have a thickness, and wherein embossing the reinforcing material may comprise embossing the reinforcing material to a depth of greater than about 40% of the reinforcing material thickness.

We claim:

1. A method of forming an absorbent body, the method comprising:

moving a first covering material in a machine direction, the first covering material having a top side and a bottom side;

moving a reinforcing material in the machine direction and combining the reinforcing material with the first covering material, the reinforcing material having a top side and a bottom side, the reinforcing material having a thickness of between 0.8 mm and 3.0 mm and a basis weight of between 25 gsm and 80 gsm;

applying absorbent material comprising superabsorbent particles to the top side of the reinforcing material;

moving a second covering material in the machine direction, the second covering material having a top side and a bottom side, and combining the second covering material with the first covering material and the reinforcing material to form a laminate structure of the first covering material, the reinforcing material, and the second covering material, with the first covering material disposed underneath the reinforcing material and the second covering material disposed on top of the reinforcing material; and embossing the laminate structure between a smooth roll and a pattern roll, the pattern roll comprising a plurality of discrete embossing surfaces disposed outward from an outer face of the pattern roll, the discrete embossing surfaces being round and spaced apart laterally and longitudinal across outer face of the pattern roll, wherein during embossing the embossing surfaces press the second covering material into the top side of the reinforcing material, wherein the laminate structure comprises greater than or equal to 90% superabsorbent material by total weight of absorbent material in the laminate structure, and wherein the superabsorbent material is disposed within the absorbent body at a basis weight of greater than 90 gsm and less than 350 gsm.

2. The method of claim 1, further comprising:

applying adhesive to one of the top side of the first covering material and the bottom side of the reinforcing material; and applying adhesive to one of the top side of the reinforcing material and the bottom side of the second covering material.

3. The method of claim 1, wherein the laminate structure comprises a laminate area, and wherein embossing the laminate structure comprises forming an embossed area greater than about 0% of the laminate area and less than about 42% of the laminate area.

4. The method of claim 1, wherein the laminate structure comprises a laminate area, and wherein embossing the laminate structure comprises forming an embossed area greater than about 5% of the laminate area and less than about 35% of the laminate area.

5. The method of claim 1, wherein the laminate structure comprises a laminate area, and wherein embossing the laminate structure comprises forming an embossed area greater than about 10% of the laminate area and less than about 30% of the laminate area.

6. The method of claim 1, wherein the laminate structure has a thickness, and wherein embossing the laminate structure comprises embossing the laminate structure to a depth of less than about 90% of the laminate structure thickness.

7. The method of claim 1, wherein the laminate structure has a thickness, and wherein embossing the laminate structure comprises embossing the laminate structure to a depth of less than about 80% of the laminate structure thickness.

8. The method of claim 1, wherein the laminate structure has a thickness, and wherein embossing the laminate structure comprises embossing the laminate structure to a depth of greater than about 40% of the laminate structure thickness.

9. The method of claim 1, wherein embossing the laminate structure comprises passing the laminate structure through an embossing nip formed by a first embossing roll and a second embossing roll, the first embossing roll comprising a plurality of embossing elements projecting from a surface of the first embossing roll where a height of the embossing elements is between about 0.8 mm and about 4.0 mm.

10. The method of claim 1, further comprising inverting the laminate structure.

11. The method of claim 1, further comprising coupling the absorbent body to an absorbent article chassis such that the first covering material forms a body-facing side of the absorbent body.

12. The method of claim 1, further comprising applying absorbent material comprising superabsorbent particles to the top side of the first covering material.

13. An embossed absorbent body comprising:

a top, liquid permeable covering material;

a bottom covering material;

a reinforcing material disposed between the top covering material and the bottom covering material; and superabsorbent material disposed within the reinforcing material in a pattern of high-SAM concentration regions and low-SAM concentration regions, the pattern of high-SAM concentration regions corresponding to a pattern of embossing surfaces used to emboss the absorbent body, wherein the embossed absorbent body comprises greater than or equal to 90% superabsorbent material by total weight of absorbent material in the absorbent body, and wherein between about 30% and about 85%, by weight, of the total amount of superabsorbent material disposed between the top covering material and the bottom covering material is stabilized within the reinforcing material, as determined according to the SAM Stabilization Location Test Method.

14. The embossed absorbent body of claim 13, wherein the high-SAM concentration regions form a pattern of discrete high-SAM concentration regions surrounded by low-SAM concentration regions.

15. The embossed absorbent body of claim 13, wherein the high-SAM concentration regions and the low-SAM concentration regions form alternating stripes within the reinforcing material.

16. The method of claim 1, wherein embossing the laminate structure forms a pattern of high-SAM concentration regions and low-SAM concentration regions within the laminate structure, and wherein the pattern of high-SAM concentration regions correspond to a pattern of the discrete embossing surfaces.

17. The method of claim 16, wherein the pattern of high-SAM concentration regions and low-SAM concentration regions comprise discrete high-SAM concentration regions surrounded by low-SAM concentration regions.

18. The method of claim 1, wherein between 30% and 85%, by weight, of the total amount of superabsorbent material disposed between the top covering material and the bottom covering material is stabilized within the reinforcing material.

19. The embossed absorbent body of claim 13, wherein between 30% and 85%, by weight, of the total amount of superabsorbent material disposed between the top covering material and the bottom covering material is stabilized within the reinforcing material.

* * * * *